(12) United States Patent
Choi et al.

(10) Patent No.: US 11,589,776 B2
(45) Date of Patent: Feb. 28, 2023

(54) NON-CONTACT BREATHING ACTIVITY MONITORING AND ANALYZING THROUGH THERMAL AND CO2 IMAGING

(71) Applicant: The Regents of the University of Colorado, a body corporate, Denver, CO (US)

(72) Inventors: Min-Hyung Choi, Superior, CO (US); Shane Transue, Arvada, CO (US); Ann Halbower, Salida, CO (US)

(73) Assignee: The Regents of the University of Colorado, Denver, CO (US)

( * ) Notice: Subject to any disclaimer, the term of this patent is extended or adjusted under 35 U.S.C. 154(b) by 632 days.

(21) Appl. No.: 16/676,346

(22) Filed: Nov. 6, 2019

(65) Prior Publication Data
US 2020/0138292 A1    May 7, 2020

Related U.S. Application Data

(60) Provisional application No. 62/756,501, filed on Nov. 6, 2018.

(51) Int. Cl.
*A61B 5/087* (2006.01)
*A61B 5/00* (2006.01)
(Continued)

(52) U.S. Cl.
CPC .......... *A61B 5/0878* (2013.01); *A61B 5/0033* (2013.01); *A61B 5/0077* (2013.01);
(Continued)

(58) Field of Classification Search
CPC ... A61B 5/0873; A61B 5/6803; A61B 5/0033; A61B 5/091; A61B 5/0878;
(Continued)

(56) References Cited

U.S. PATENT DOCUMENTS

| 4,928,703 A | 5/1990 | Wong |
| 4,955,946 A | 9/1990 | Mount et al. |

(Continued)

OTHER PUBLICATIONS

Abbas, Abbas K. et al., "Intelligent Neonatal Monitoring Based on a Virtual Thermal Sensor," BMC Medical Imaging, vol. 14, No. 9, p. 13 pages, 2014.

(Continued)

*Primary Examiner* — Phi Hoang

(57) ABSTRACT

Various embodiments of the disclosed technology present a structural foundation for volumetric flow reconstructions for expiratory modeling enabled through multi-modal imaging for pulmonology. In some embodiments, this integrated multi-modal system includes infrared (IR) imaging, thermal imaging of carbon dioxide ($CO_2$), depth imaging (D), and visible spectrum imaging. These multiple image modalities can be integrated into flow models of exhale behaviors enable the creation of three-dimensional volume reconstructions based on visualized $CO_2$ distributions over time, formulating a four-dimensional exhale model which can be used to estimate various pulmonological traits (e.g., breathing rate, flow rate, exhale velocity, nose/mouth distribution, tidal volume estimation, and $CO_2$ density distributions). Various embodiments also enable the accurate acquisition of numerous pulmonary metrics that are then stored within distributed systems for respiratory data analytics and feature extraction through deep learning embodiments.

24 Claims, 32 Drawing Sheets

(51) Int. Cl.
| | |
|---|---|
| A61B 5/091 | (2006.01) |
| G16H 30/40 | (2018.01) |
| G06T 5/10 | (2006.01) |
| G06T 7/00 | (2017.01) |
| G06T 17/10 | (2006.01) |

(52) U.S. Cl.
CPC ............ *A61B 5/0873* (2013.01); *A61B 5/091* (2013.01); *A61B 5/6803* (2013.01); *G06T 5/10* (2013.01); *G06T 7/0012* (2013.01); *G06T 17/10* (2013.01); *G16H 30/40* (2018.01); *A61B 2560/0431* (2013.01); *A61B 2562/0271* (2013.01); *G06T 2207/10024* (2013.01); *G06T 2207/10028* (2013.01); *G06T 2207/10048* (2013.01); *G06T 2207/20221* (2013.01)

(58) Field of Classification Search
CPC .......... A61B 5/0077; A61B 2560/0431; A61B 2562/0271; A61B 5/01; A61B 5/0816; A61B 2576/00; A61B 5/082; G16H 30/40; G16H 50/50; G06T 7/0012; G06T 5/10; G06T 2207/10028; G06T 5/50; G06T 2207/20221; G06T 7/11; G06T 17/10; G06T 2207/10048; G06T 2207/10024

See application file for complete search history.

(56) References Cited

U.S. PATENT DOCUMENTS

| | | | | |
|---|---|---|---|---|
| 8,500,451 | B2 * | 8/2013 | Bronstein | G06T 17/00 434/262 |
| 8,520,074 | B2 | 8/2013 | Wang et al. | |
| 8,554,490 | B2 * | 10/2013 | Tang | A61B 8/13 382/128 |
| 8,647,605 | B2 * | 2/2014 | Mangat | A61K 49/0041 424/9.6 |
| 8,715,202 | B2 | 5/2014 | Cardoso et al. | |
| 8,790,269 | B2 | 7/2014 | Xu et al. | |
| 9,697,599 | B2 | 7/2017 | Prasad et al. | |
| 2003/0025081 | A1 | 2/2003 | Edner et al. | |
| 2004/0111014 | A1 | 6/2004 | Hickle | |
| 2009/0048523 | A1 * | 2/2009 | Schlagheck | A61B 5/0073 600/473 |
| 2012/0087469 | A1 * | 4/2012 | Masuo | A61B 6/4441 378/115 |
| 2013/0079658 | A1 * | 3/2013 | Cardoso | G01N 33/497 600/532 |
| 2013/0181836 | A1 | 7/2013 | Cardoso et al. | |
| 2016/0156880 | A1 * | 6/2016 | Teich | H04N 5/33 348/82 |
| 2016/0354007 | A1 * | 12/2016 | Gärber | A61B 5/7271 |
| 2017/0245936 | A1 * | 8/2017 | Kanade | A61B 5/062 |
| 2018/0190017 | A1 * | 7/2018 | Mendez | G06T 17/00 |
| 2019/0261891 | A1 * | 8/2019 | Ahmad | A61B 5/087 |
| 2019/0340671 | A1 * | 11/2019 | Tran | A45D 44/005 |
| 2021/0169375 | A1 * | 6/2021 | Slepian | A61B 5/6823 |

OTHER PUBLICATIONS

Al-Khalidi, F. Q. et al., "Tracking Human Face Features in Thermal Images for Respiration Monitoring," 2010 IEEE/ACS International Conference on Computer Systems and Applications, 7 pages, May 16-19, 2010.

Al-Khalidi, Farah Q. et al., "Respiration Rate Monitoring Methods: A Review," Pediatric Pulmonology, 48 pages, 2011.

Al-Obaisi, Fida et al., "Pattern Recognition of Thermal Images for Monitoring of Breathing Function," International Journal of Control and Automation, vol. 8, No. 6, pp. 381-392, 2015.

Aoki, Hirooki et al., "Study on Respiration Monitoring Method Using Near-Infrared Multiple Slit-Lights Projection," IEEE International Symposium on Micro-NanoMechatronics and Human Science, pp. 291-296, Nov. 7-9, 2005.

Chekmenev, S. Yu et al., "Non-Contact, Wavelet-Based Measurement of Vital Signs Using Thermal Imaging," ICGST International Journal on Graphics, Vision and Image Processing, vol. 6, No. 2, pp. 25-30, 2006.

Fe, Jin et al., "Analysis of Breathing Air Flow Patterns in Thermal Imaging," Proceedings of the 28th IEEE EMBS Annual International Conference, pp. 946-952, Aug. 30-Sep. 3, 2006.

Fe, Jin et al., "Imaging Breathing Rate on the CO2 Absorption Band," Proceedings of the 2005 IEEE Engineering in Medicine and Biology 27th Annual Conference, pp. 700-705, Sep. 1-4, 2005.

Hanawa, Dai et al., "Basic Study on Non-Contact Measurement of Human Oral Breathing by Using Far Infra-Red Imaging," IEEE, pp. 681-684, 2016.

Hsu, Cheung-Hwa et al., "Design and Clinic Monitoring of a Newly Developed Non-Attached Infant Apnea Monitor," Biomedical Engineering—Applications, Basis & Communications, vol. 17, pp. 126-134, Jun. 2005.

Jaffe, Michael B., "Infrared Measurement of Carbon Dioxide in the Human Breath: 'Breathe-Through' Devices From Tyndall to the Present Day," Anesthesia & Analgesia, vol. 107, No. 3, pp. 890-904, Sep. 2008.

Murthy, Jayasimha et al., "Thermal Infrared Imaging: A Novel Method to Monitor Airflow During Polysomnography," SLEEP, vol. 32, No. 11, pp. 1521-1527, 2009.

Murthy, Ramya et al., "Touchless Monitoring of Breathing Function," Proceedings of the 26th Annual International Conference of the IEEE EMBS, pp. 1196-1199, Sep. 1-5, 2004.

Prochazka, Ales et al., "Breathing Analysis Using Thermal and Depth Imaging Camera Video Records," Sensors, vol. 17, 10 pages, Jun. 16, 2017.

Rutz, F. et al., "Imaging Detection of CO2 Using a Bispectral Type-II Superlattice Infrared Camera," 11th International Conference on Quantitative InfraRed Thermography, 7 pages, Jun. 11-14, 2012.

Vollmer, M. et al., "IR Imaging of CO2: Basics, Experiments, and Potential Industrial Application," SENSOR + TEST Conferences 2011, pp. 59-64, 2011.

Zhu, Zhen et al., "Tracking Human Breath in Infrared Imaging," Proceedings of the 5th IEEE Symposium on Bioinformatics and Bioengineering, 5 pages, 2005.

* cited by examiner

FIG. 21A (a) Heat image
FIG. 21B (b) Heat flow image
FIG. 21C (c) Background image
FIG. 21D (d) Background flow image FIG. 22A (a) XOR Flow Image FIG. 22B (b) Dense Optical Flow FIG. 22C (c) Negative Exhale FIG. 23A (a) X Derivative (dx)
FIG. 23B (b) Y Derivative (dy)
FIG. 23C (c) Flow Normals
FIG. 23D (c) Flow Intensity

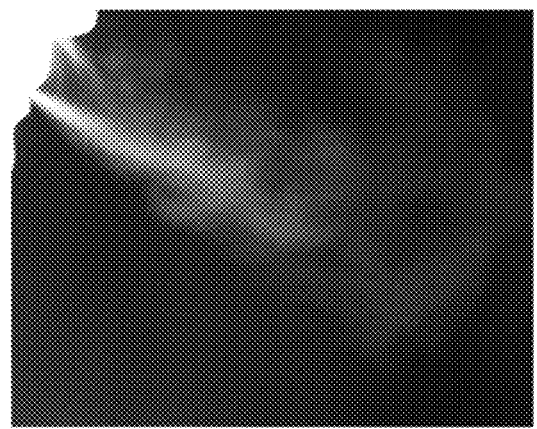
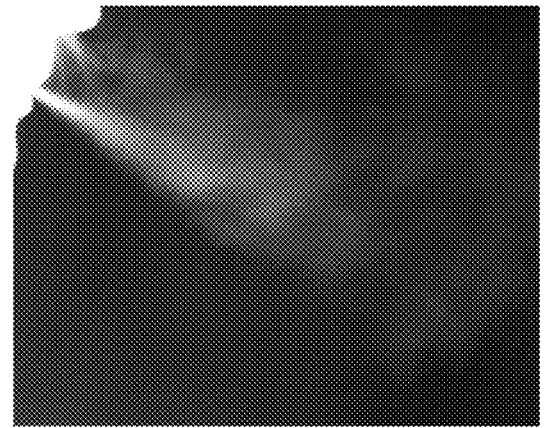
FIG. 27

NON-CONTACT BREATHING ACTIVITY MONITORING AND ANALYZING THROUGH THERMAL AND CO2 IMAGING

CROSS-REFERENCE TO RELATED APPLICATIONS

This application claims priority to U.S. Provisional Application Ser. No. 62/756,501 filed Nov. 6, 2018, which is incorporated herein by reference in its entirety for all purposes.

STATEMENT REGARDING FEDERALLY FUNDED RESEARCH

This invention was made with government support under grant number ACI-1602428 awarded by National Science Foundation. The government has certain rights in the invention.

TECHNICAL FIELD

Various embodiments of the present technology generally relate to systems and methods for monitoring breathing activity and identifying various pulmonary conditions. More specifically, some embodiments of the present technology relate to non-contact breathing activity monitoring and analyzing through thermal and $CO_2$ imaging.

BACKGROUND

Evaluating objective reconstructions of vortex behaviors within turbulent flows is an open problem within computational fluid dynamics due to reference frame dependent flow behaviors. Recent flow visualization techniques have proposed visualizations of vortex behavior through optimally local reference frame optimization for reconstructing complex vortex flows. Other flow reconstruction techniques attempt to build models of complex gas flows through refraction-based Background-oriented Schlieren methods or through Light-Path approximations captured through multiple imaging devices using visible light wavelengths. These techniques represent a divergence from traditional tracer-based method such as Particle Image Velocimetry (PIV) that requires discrete cross-correlation of discrete tracer particles which is impractical for our clinical domain.

Accurate non-contact respiratory analysis has recently gained popularity within the domains of wireless signal processing and computer vision to automate and significantly broaden the class of quantitative respiratory metrics that non-contact methods can reliably address. Numerous techniques exist for both contact and non-contact respiratory analysis. However, traditional methods indirectly infer breathing behaviors or utilize correlation functions for respiratory analysis. Techniques within computer vision have introduced thermal infrared cameras with spectral filters for $CO_2$ imaging for respiratory analysis. However, the applicability of these techniques to comprehensive respiratory analysis is severely underdeveloped and the adoption of these methods has been very limited.

This is due to three primary factors shared between most prior vision-based techniques: (1) prior objectives only emphasize simple quantitative measures such as respiratory rate within limited Regions of Interest (RoI) and strength, limiting potential high-level behavioral analysis, (2) prior devices lack the sensitivity required to monitor subtle density variances and complex flow behaviors for identifying respiratory conditions, and (3) frame-rate limitations inhibit the ability to accurately capture rapid and turbulent respiratory behaviors. As such, there are a number of challenges and inefficiencies created in traditional respiratory analysis systems. It is with respect to these and other problems that embodiments of the present invention have been made.

SUMMARY

Various embodiments of the present technology generally relate to systems and methods for monitoring breathing activity. More specifically, some embodiments of the present technology relate to non-contact breathing activity monitoring and analyzing through thermal and $CO_2$ imaging. Various embodiments provide for systems and methods for the extraction of clinically meaningful metrics for respiratory analysis. This includes, but is not limited to, the reconstruction of exhale flows to obtain tidal volume estimates, the identification of the separation between nose and mouth exhale flows to measure nose/mouth distribution, and both the velocity and strength of exhale flows.

Moreover, some embodiments provide for the 3D reconstruction of turbulent exhale flows through the use of the $CO_2$ thermal imaging camera. Some embodiments of this process can incorporate recording the exhale flow, extracting the flow characteristics, and spatial metrics required to provide a direct measurement of the exhale per breath. A geometrically consistent estimation of the approximate flow volume can be reconstructed on a per-frame basis to provide an estimate of the patient's tidal volume.

Various embodiments use inverse thermal $CO_2$ segmentation techniques to provide a method for robust exhale tracking for images with complex backgrounds for clinical applications. Through the use of multiple imaging algorithms, various embodiments allow the exhale distribution to be tracked from several camera angles including those that include the patient's face or other complex thermal signatures within the background.

Some embodiments incorporate several devices to facilitate a robust multi-modal analysis method for remote respiratory analysis. Some embodiments include: a thermal camera tuned to the $CO_2$ spectral absorption band (3-5 micron), a depth imaging camera that provides sufficient resolution for human and face tracking, a laser transmitter (Tx) and receiver (Rx) for distance calibration, and a traditional visible-spectrum (RGB) camera. These components can be housed within a single housing that provides a targetable vision system. The orientation and position of this housing can be defined through inverse kinematics within the adjustable segments. This allows some embodiments of the devices to be precisely aligned to the target viewing angle that can maximize the number of metrics that can be extracted with the highest possible accuracy.

Embodiments of the present invention also include computer-readable storage media containing sets of instructions to cause one or more processors to perform the methods, variations of the methods, and other operations described herein.

Some embodiments provide for a method for analyzing pulmonological functions. The method can include obtaining a thermal image that may or may not include the subject and surrounding region, isolating the pulmonological behavior of the subject by identifying and tracking the exhale fluid dynamics exhibited by the intensity of the pixels that correspond to $CO_2$ gas flow behaviors. In some embodiments, flow patterns can be used to identify and track exhale behaviors from the surrounding thermal objects. The flow is then used to construct a 3D representation of the flow through the assistance of the depth camera that provides units to the volumetric measurements of the exhale flow.

In some embodiments, pixel intensities can be used to represent a coupled relationship between thermal energy and $CO_2$ emissivity. Thermal heat sources behind the exhale region interfere with the exhale signal due to the combined infrared wavelengths detected from the background heat source and the energy of the exhaled $CO_2$ region. This creates a mixed signal that represents the IR emission from both sources. The exhale signature flow can be extracted from this mixed data. Various embodiments of the segmentation method can extract flow characteristics to localize the exhale and then separates the exhale component from background sources. For example, some embodiments can identify the background thermal ($T_b$) and $CO_2$ components ($T_{co2}$) represented by the pixel values within each captured image. The assumed thermal intensity of each pixel in the fused image is represented by $p=T_b+T_{co2}$. The result of the signal separation process is to identify the proportional measurement of $T_b$ and $T_{co2}$.

Depth values can be correlated between the thermal $CO_2$ and depth images to provide depth estimates for the pixels identified as belonging to the exhale flow. This provides a spatial measurement of the exhale pixels and the distance measurement between adjacent pixels. The process of separating exhale behaviors requires multiple fluid flow computations with different image scaling factors. The first pass can identify warmer exhale flows in front of backgrounds with less thermal energy and the second pass can identify cooler exhale flows in front of warmer objects (such as the face or body). The results of these two passes can be combined, in various embodiments, to create a single exhale flow. This can be used to clearly identify exhale flows regardless of the background object from which the IR signal may occlude the exhale.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the scope of the present invention. Accordingly, the drawings and detailed description are to be regarded as illustrative in nature and not restrictive.

BRIEF DESCRIPTION OF THE DRAWINGS

Embodiments of the present technology will be described and explained through the use of the accompanying drawings in which:

FIG. 27 illustrates two subsequent exhale frames based on grayscale pixel intensity in accordance with various embodiments of the present technology;

Figure 1A:
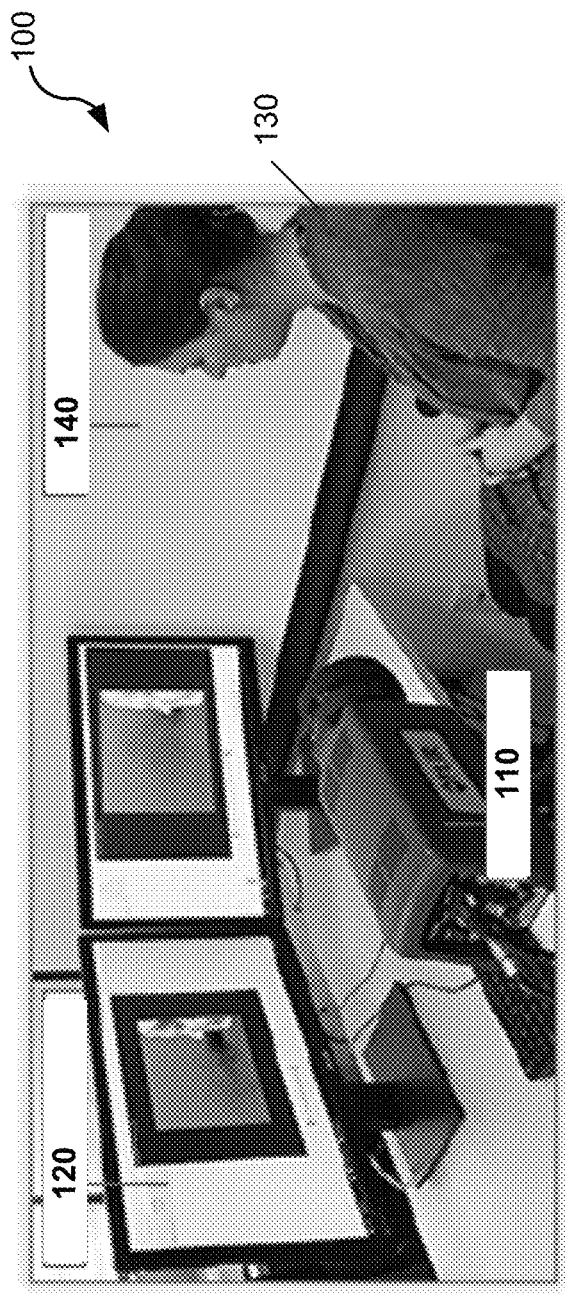
FIG. 1A illustrates an example of a system for $CO_2$ imaging in accordance with one or more embodiments of the present technology.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

Various embodiments of the present technology generally relate to systems and methods for monitoring breathing activity. More specifically, some embodiments of the present technology relate to non-contact breathing activity monitoring and analyzing through depth and thermal imaging targeting $CO_2$ visualization to obtain objective measurements of flow behaviors. Conventional breath monitoring systems need to place devices on patients, which causes discomfort, alters natural breathing, and may not be applicable for long term monitoring. Moreover, the primary evaluation criteria within respiratory analysis revolves around the collection of a limited set of quantitative metrics such as breathing rate, behavioral flow analysis, and tidal volume estimates.

Extensive research has culminated numerous contact and non-contact methods that obtain these metrics with promising levels of accuracy. However, based on these existing methods, all current respiratory evaluation is performed using indirect methods, that is, they infer measurements through secondary signals such as visible chest movements, vibration, pressure, acceleration, or sound. Prior methods using spectral analysis for $CO_2$ visualization have introduced a direct means of evaluating respiratory behaviors using direct exhale measurements, but have been largely limited to obtaining measurements of breathing rate. There have been prior methods similar to this form of direct analysis, where the exhaled $CO_2$ is measured using a limited Region of Interest (RoI) to obtain measurements of breathing rate based on the temperature fluctuation within this region. While existing methods are related, they are limited to only providing an evaluation or measurement of breathing rate.

Stemming from the initial introduction of thermal cameras within industrial applications for identifying the spectral signature of specific gases, carbon dioxide ($CO_2$) imaging has been primarily applied to exhale visualization and has only recently been adapted for respiratory analysis. Still, while incremental progress has been made towards generating behavioral metrics for clinical respiratory analysis, the primary information obtained using existing methods revolves around observations such as breathing rate and $CO_2$ concentration levels. However, for clinical respiratory analysis these metrics fail to provide meaningful contributions to diagnosing conditions and can be obtained using less complex and cheaper alternative devices.

Due to this, thermal imaging for direct $CO_2$ analysis has had limited penetration within the medical community. One of the primary challenges for this adaptation is the potential cost incurred from using a complex thermal camera must outweigh the benefits and metrics obtained from using other simple and inexpensive devices. Therefore, the introduction of additional, clinically meaningful metrics and behavior analysis methods must be addressed through the use of new $CO_2$ imaging techniques to justify both the cost and system complexity required to deploy this method as a viable alternative to these smaller, effective, and cheaper monitoring devices.

In contrast, various embodiments of the present technology present a comprehensive system of algorithms and hardware solutions that define two system designs for continuously monitoring of exhale flows using $CO_2$ imaging for pulmonary and respiratory analysis. Various embodiments provide the addition of several quantitative metrics for natural breathing that cannot be obtained using existing solutions including natural exhale behaviors, tidal volume, nose-to mouth distribution, velocity, strength, and pulmonary condition evaluation.

Various embodiments use a specialty thermal and $CO_2$ camera to capture images and videos of human exhale and to extract clinically valuable information in a non-invasive way. As a result, various embodiments allow for non-contact analysis of various breathing activities including breathing rate, speed, strength, tidal volume, nose/mouth distribution, and $CO_2$ concentration out of exhale, lung efficiency, and obstructive breathing which can be used for various breathing/pulmonary related diseases diagnosis.

To develop a device for directly analyzing turbulent $CO_2$ exhale flows, some embodiments utilize a hyper-sensitive thermal camera that contains an embedded spectral filter that directly targets the $CO_2$ spectral band (3-5 [μm]). In some embodiments, the device provides raw $CO_2$ count images that contain the infrared wavelength activation counts within the $CO_2$ absorption band. Through the development of these imaging methods and our direct measurements of breathing behavior, some embodiments use a new vector in vision-based clinical respiratory analysis. This includes direct flow and thermal analysis for subtle alternations in airflow related to asthma, Chronic Obstructive Pulmonary Disease (COPD), developmental conditions related to nose and mouth breathing distributions, cognitive function, sleep apnea, and Sudden Infant Death Syndrome (SIDS).

In some embodiments, a method for evaluating pulmonological function for a variety of different metrics can be used. The natural behavior of turbulent exhale flow, evaluation of natural breathing unimpeded by device attachments or tubes, nose to mouth breathing distribution, natural shifts of respiratory behaviors between nose/mouth and nostrils, exhale velocity, and subtleties or natural alterations of exhale behaviors due to the influence of any pulmonological condition. This also includes standard metrics: breathing rate, tidal volume, and $CO_2$ density.

Flow characteristics can be extracted from the combined image modalities to provide a non-contact form of exhale analysis. This enables natural breathing which is defined as an uninhibited or restricted form of exhale directly from the nose and mouth. This measure approximates the flow in Liters per second (L/s) during the expiratory phase of normal breathing. Natural fluctuations between the mouth and nose and between nostrils are identified as a distribution of the exhale path. The portion of exhale in this distribution are measured using the flow reconstruction. From the full or partial construction of the flow, the distribution is represented as a percentage (%) of the flow between the mouth and each nostril. This also covers monitoring natural shifts in respiratory behaviors between the mouth and each nostril. The generation of the flow model may be obtained in some embodiments from each time-step using the changes in intensity value related to the optical flow of the fluid movement. From this information, changes in the spatial distribution of the exhale is measured with the assistance of the depth image that is used to provide estimates of the distance between adjacent pixels $D(P_{adj})$. Based on the time between captured frames (dt), the velocity is computed based on a dense representation of a 3D vector field that represents the flow velocity at each pixel. The velocity for each voxel in the reconstruction is then defined as: $\vec{v} = D(P_{adj})/dt$. The velocity is measured in meters per second (m/s).

Respiratory rate can be computed in some embodiments as a function of the exhale flow model. As $CO_2$ is expelled, the computed flow and volume can be used to provide rate as a measure of the time between the transition between inspiratory and expiratory states. This can be used to form a continuous waveform and scalar unit of the breathing rate. The unit of the breathing rate is recorded in Breathes Per Minute (BPM).

The defined flow model can provide a basis on which the exhaled $CO_2$ permeates through the air as it dissipates. This describes the spatial representation of how the gas forms a volumetric representation of the exhale within each recorded frame. The flow field that describes the expansion and dissipation of the exhaled gas is used to formulate a sparse representation of the exhale volume based on temporal slices of the exhale captured in each multi-modal image. Using the distance between adjacent pixels as the base unit, the volume of the exhale model can be directly measured in meters cubed ($m^3$) which is then converted to Liters (L).

Density of the $CO_2$ contained in each frame of the recorded exhale behavior is obtained through training a deep learning model on the correlation between pixel intensity, flow velocity, and a dissipation model that represents how the exhaled $CO_2$ loses thermal energy and dissipates into open atmosphere as a pressure measurement in millimeters of Mercury (mmHg) or Pascal (Pa). In some embodiments, a condition diagnosis can be assisted through the analysis of exhale flow behaviors and their deviation from normal behaviors as defined by the provided set of metrics.

Flow models can be captured and stored with respect to a specific subject. This includes the original fused image sequence capturing during the real-time monitoring of the subject, the flow and volumetric reconstruction of the exhale stored as a sparse representation of voxel information, and associated respiratory metrics extracted from these models. The stored collection of subject-specific models and pulmonary function measurements, the model can be used to statistically analyze and predict abnormalities in new query models. Status of the query model can be evaluated with respect to a collection of n existing models to identify statistical outliers in the flow patterns or metric values as they deviate or match the characteristics of existing models. The accuracy of the proposed system grows with the collection of new models, each of which further populates a closer approximation of all common exhale behaviors. Traits shared between similar models can be used to identify subtle similarities between subjects that exhibit symptoms of related pulmonological conditions.

In some embodiments, subconscious breathing behaviors can be monitored for extended periods of time including overnight studies where the subject is in the immediate proximity of the device. Due to movement of the subject during the monitoring period, the device may need to be adjusted to account for obtaining an optimized viewing angle. The device can be adjusted in an automated way to avoid continuous intervention between the user and device to capture subconscious breathing behavior. Subconscious breathing behaviors are monitored and tracked to formulate subject dependent breathing profile stored within a remote client.

Depth and infrared images can be integrated as inputs to a 4D model of the exhale behaviors that includes volumetric modeling of the pulmonological expiratory behavior, dissipation modeling, and detailed flow reconstructions. This 4D model is composed of the sequential reconstruction of 3D volumetric and flow representations extracted from the thermal and depth images. Some embodiments can extract pulmonological characteristic and physical representation of the behavior and generates a per-subject 4D model used to measure standard pulmonological metrics including breathing rate, velocity, distribution, and tidal volume. A 4D model can be obtained from each subject for each unique exhale. This results in the collection of a large number of individual exhale models that can be used to develop a profile that is tied to the subject and their own subtle pulmonological traits.

The 4D model construction process used in some embodiments can include: (1) obtain thermal $CO_2$ intensity, depth, and RGB images, (2) integrate or fuse these images into an aggregate of the image modalities, (3) identify adjacent pixel distances $D(P_{adj})$, (4) compute apparent exhale optical flow, (5) extrapolate flow behaviors into three-dimensions from the 2D aggregate image, (6) expand the flow behaviors into a volume by a sparse voxel representation.

Due to the limited flow and volume related to children and infant exhale, secondary image-processing algorithms are required to enhance the apparently flow behaviors. To do this the flow behaviors are isolated and separated from background IR emitting sources. To improve the detection of minute exhale traces, models that predict flow behavior based on smaller movements are used to predict and enhance flow behaviors. Some embodiments can evaluate the facial structure and airway development in children, infants, and neonates. This method is also capable of identifying acute respiratory failure and other less severe conditions such as central and obstructed apnea in children.

Building on the aggregate image that contains both the exhaled $CO_2$ and respiratory flow behaviors and the depth image of the chest and face, exhale behaviors are correlated with chest movement to identify potential abnormalities related to breathing for children, infants, and neonates. Relating chest movement to exhaled $CO_2$, a predictive model can be formulated to identify and detect obstructed breathing. The model reflects chest movement as a factor of effort towards a smooth inspiration-expiration cycle and the exhaled $CO_2$ represents the actual airflow expelled by the lungs expressed as a 4D flow volume model.

Various embodiments of the present technology provide for a wide range of technical effects, advantages, and/or improvements to computing systems and components. For example, various embodiments include one or more of the following technical effects, advantages, and/or improvements: 1) integrated use of multiple imaging modalities to generate multiple pulmonary metrics (e.g., nose/mouth distribution, velocity, dissipation, behavioral characteristics, and even insight into lung efficiency in controlled environments); 2) integrated use of automation techniques to dynamically move imaging system to provide a consistent view of exhale gas flow; 3) use of unconventional and non-routine computer operations to provide an accurate turbulent exhale flow analysis, 4) use of unconventional and non-routine computer operations to model direct flow behaviors required for identifying potential respiratory conditions; 5) introduction of a new methodology for identifying condition-trait signatures using clinical non-contact respiratory analysis with an aim of associating exhale flow behaviors with common pulmonary conditions and diseases; 6) cross-platform integration of machine learning to more efficiently identify breathing patterns; 7) changing the manner in which a computing system reacts to processing of imaging data; 8) provides the separation and semantic identification of each component of the mixed thermal and $CO_2$ signals from the detected exhale flow including the separation from other background heat sources to uniquely identify the $CO_2$ volume and density within open-air; and/or 9) for the detection and visualization of the flow and dynamic behavior of other molecules in the exhale gas, the range of spectroscopic wavelength can be adjusted and filtered to uniquely identify the target.

In the following description, for the purposes of explanation, numerous specific details are set forth in order to provide a thorough understanding of embodiments of the present technology. It will be apparent, however, to one skilled in the art that embodiments of the present technology may be practiced without some of these specific details.

The techniques introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions which may be used to program a computer (or other electronic devices) to perform a process. The machine-readable medium may include, but is not limited to, floppy diskettes, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions.

The phrases "in some embodiments," "according to some embodiments," "in the embodiments shown," "in other embodiments," and the like generally mean the particular feature, structure, or characteristic following the phrase is included in at least one implementation of the present technology, and may be included in more than one implementation. In addition, such phrases do not necessarily refer to the same embodiments or different embodiments.

Overview

Figure 1C:
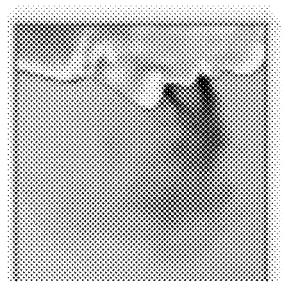
FIGS. 1B-1C illustrates examples of a dense exhale flow analysis through optimized $CO_2$ imaging for illustrating unique respiratory behaviors of multiple individuals in accordance with various embodiments of the present technology.
Figure 1B:
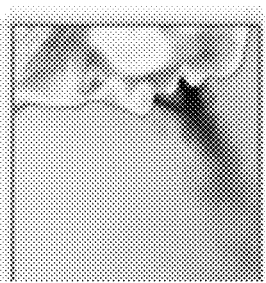

FIG. 1A illustrates an example of a system 100 for $CO_2$ imaging in accordance with one or more embodiments of the present technology. In the embodiments illustrated in FIG. 1A, the system can include a $CO_2$ imaging device 110, a computing system to generate a real-time stream 120 of exhale flow of patient 130 against matte projection or generalized background environment 140. FIGS. 1B-1C illustrates examples of a dense exhale flow analysis through optimized $CO_2$ imaging for illustrating unique respiratory behaviors of multiple individuals in accordance with various embodiments of the present technology.

While not illustrated in FIG. 1A, various embodiments of the system can include an infrared (IR) thermal camera that performs a spectral band-pass filter tuned to a 3-5 [um] interval to limit incoming wavelengths to that relevant to the visualization of $CO_2$, an infrared camera that provides depth imaging, and a high resolution visible spectrum (RGB) camera. These devices can be connected to an external workstation or mobile device, or wearable solution that performs fusion and other algorithms required for respiratory analysis and metric extraction. In accordance with various embodiments, the thermal, depth, and RGB cameras may be interchangeable with any set of devices that image the corresponding intervals of the electromagnetic spectrum required to obtain the described signals. In some embodiments, the thermal, depth, and visible spectrum camera can be housed within a single device to provide a targetable vision system that include mobile or wearable solutions.

Some embodiments provide for a self-contained set of multiple sensors that are fused with the objective of providing non-contact respiratory analysis based on exhale flow and volume characteristics which can be collected over long-term durations. Computation of the device can be based on a combination of local processing to perform a subset of operations related to the fusion of multiple imaging modalities which can then be connected to a workstation computer or connected to a server computer acting as part of a distributed system.

The processing techniques used by various embodiments can be device independent, where each of the three imaging devices can be interchanged with equivalents, assuming sufficient resolution by each device to image the face and surrounding region. Some embodiments use pixel intensity values received from the infrared imaging device that measures values based within the required chemical emitted wavelength interval. Intensity values of pixels can be used to measure fluid flow characteristics of the exhale behavior. Flow behavior can then be identified independently of exact pixel values and characterized by changes of apparently flow measurements to reconstruct 4D models of exhale episodes. Some embodiments can create a 4D model that is composed of three-dimensional flow and volume information extracted through relative pixel measurements over time.

Exhale behavior and measurements may be obtained independent of image content through the isolation and extraction of flow behaviors. Localization and reconstruction of the exhale flow behaviors can be separated from identifiable objects within the background. Similarly, flow and volume reconstructions can be obtained through processing a sequence of images that compose a video stream of the thermal $CO_2$, depth, and RGB images. In some embodiments, the targetable vision system may be constrained by view objectives that define optimized viewing directions of the housing by modifying its position and orientation through inverse kinematics. As such, some embodiments techniques for orienting the device to obtain an ideal view of the exhale behaviors in any environment.

Figure 2A:
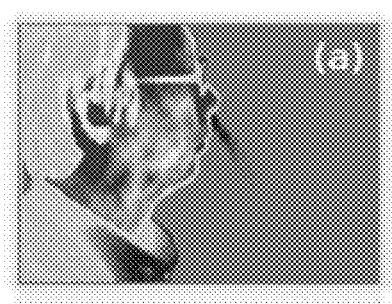
FIG. 2A illustrates a result from a traditional thermal respiratory $CO_2$ imaging device.
Figure 2B:
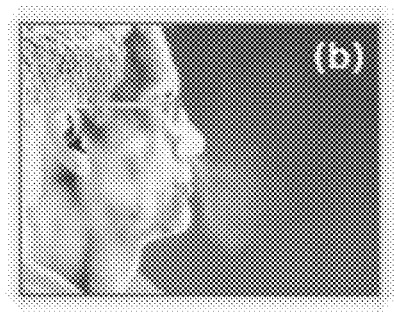
FIG. 2B illustrates an example of direct reconstruction of the experimental setup produce by various embodiments of the present technology.
Figure 2C:
FIG. 2C illustrates a detailed example of an exhale visualization result produced by one or more embodiments of the present technology.

FIG. 2A illustrates a result from a traditional thermal respiratory $CO_2$ imaging device. FIG. 2B illustrates an example of direct reconstruction of the experimental setup produce by various embodiments of the present technology. FIG. 2C illustrates a detailed example of an exhale visualization result produced by one or more embodiments of the present technology. As such various embodiments of the present technology enable new metrics which significantly diverges from existing $CO_2$-based imaging techniques in both the level of analysis and the resolution of modeling, as shown in FIG. 2B, as compared with the prior result introduced within shown in FIG. 2A.

Exhale flow behavior modeling provides a basis for evaluating high-level respiratory characteristics based on a set of observable phenomena that is not facilitated by current monitoring techniques. This includes momentary fluctuations within exhale streams that inherently contribute to secondary flow behaviors associated with obstructed breathing, subtle changes between nose-mouth breathing distributions, lung functionality, and the ability to identify abnormal exhale $CO_2$ signatures. To extend respiratory analysis to include these metrics, some embodiments use a dense flow reconstruction process including: (1) flow estimation through dense optical flow, (2) heuristic-based flow slice extrapolation, and (3) provide a volumetric sparse scalar field representation of recorded exhale behaviors for extended monitoring periods.

Dense Exhale Modeling

In accordance with some embodiments, carbon dioxide density images can be obtained through a camera and can be characterized by the projection of volumetric densities of the observable gas flows with general infrared radiation, filtered to the spectral wavelength interval required for $CO_2$ imaging. To maximize clarity in this measurement, some embodiments improve the sensitivity of our recording model by adding a thin matte surface parallel to the imaging plane that contains a uniform heat distribution.

Figure 3:
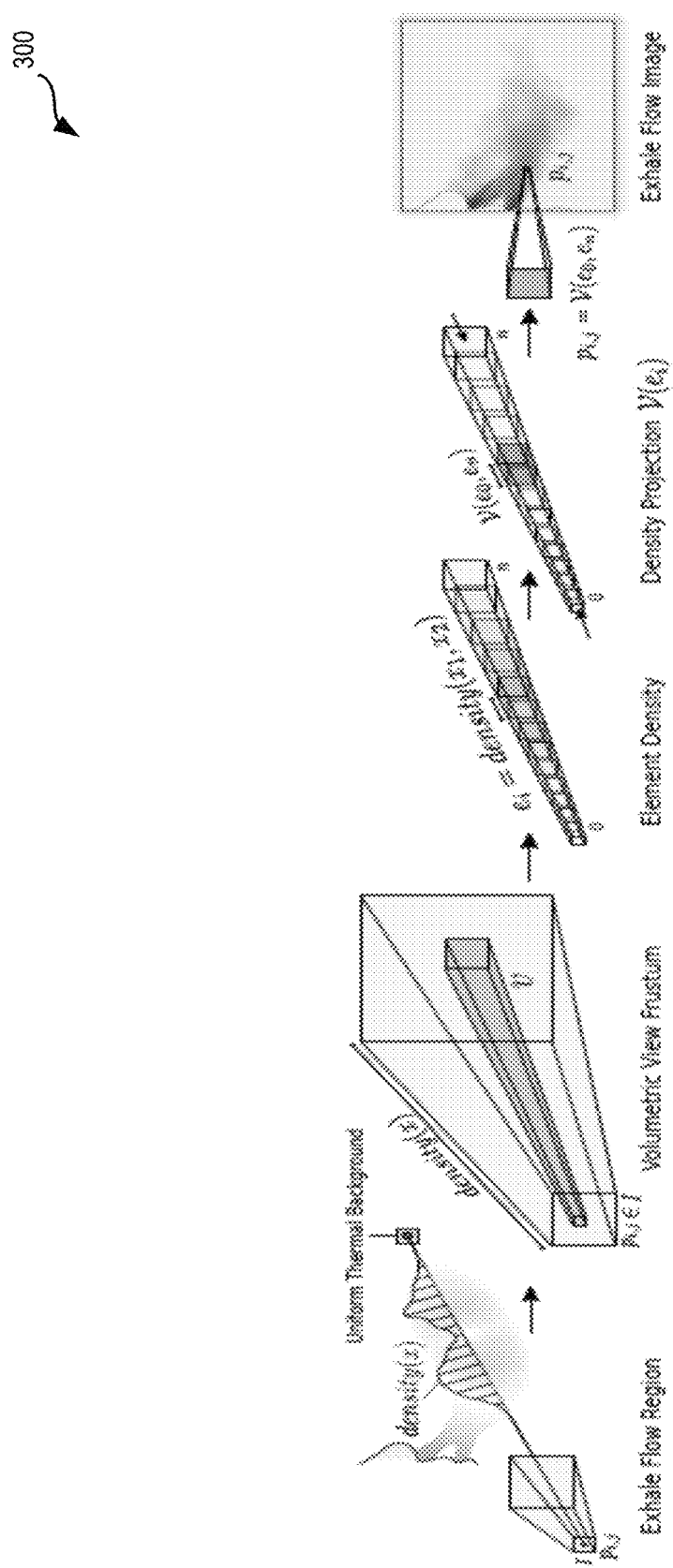
FIG. 3 illustrate an example of volumetric and density modeling of the $CO_2$ exhale region defined by a view frustum of an imaging device in accordance with some embodiments of the present technology.

FIG. 3 illustrates an example of volumetric and density modeling 300 of the $CO_2$ exhale region defined by a view frustum of an imaging device in accordance with some embodiments of the present technology. The exhale flow region contains a non-linear $CO_2$ concentration distribution function density over distance x. Each individual pixel $p_{i,j}$ represents a continuous volume through which the exhale flows. Based on the density value evaluated at each element $e_i$, the final value of pixel $p_{i,j}$ is the projection of all element densities within v.

Through the view frustum of the camera shown in FIG. 3, some embodiments model the continuous volume V of element e for each corresponding pixel $p_{i,j}$ from this surface to the image plane I as a discrete set of n elements with an unknown density distribution function density as a function of distance x. This per-element density function V (e) can be projected to the image plane at pixel $P_{i,j}$ resulting in an irreversible loss of this distribution. Some embodiments use a model based on heuristic approximations of the inverse $V^{-1}(e_i)$ of this volumetric projection to determine the per frame scalar density value $v_{i,j,k}$ within a sparse voxel grid:

$$v_{i,j,k} = V^{-1}(p_{i,j}) = V^{-1}\left[\sum_{i=1}^{n} \text{density}(e_i)\right] \ \forall\ p \in I$$

Since the consolidation of this density volume to an image representation is unrecoverable due to the projection of the per-element densities, the reconstruction is inherently limited to an approximation of the original volume but preserves overall flow behavior. This instantaneous flow behavior is then represented within the 3D voxel grid for each captured frame. The continuous collection of subsequent frames constitutes the basis for generating 4D exhale models.

Figure 4:
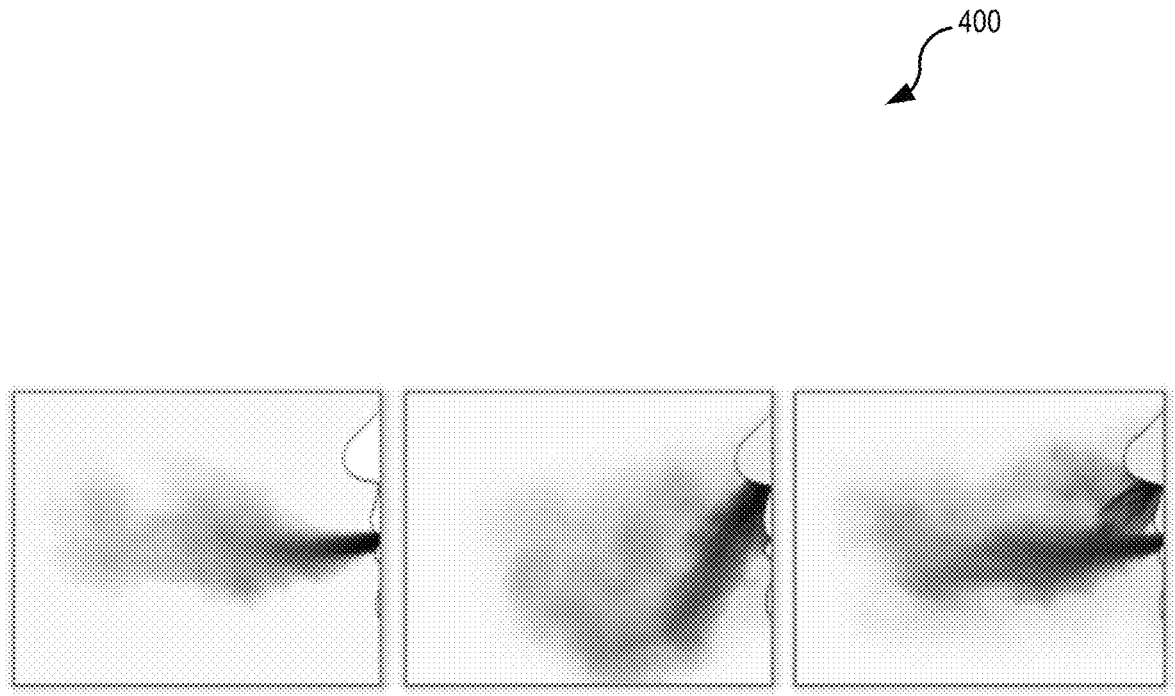
FIG. 4 illustrates an example of recorded turbulent exhale flow from the mouth (left), nose (center), and both nose and mouth simultaneously (right) created by various embodiments of the imaging process.

FIG. 4 illustrates an example of the resulting intensity images 400 of the exhale obtained through this method, demonstrating multiple dense turbulent flows. Due to this result, some embodiments do not limit analysis to an individual sub-image RoI. Some embodiments consider the entire exhale region to model both behavioral characteristics and diffusion properties of exhale sequences to build a per-patient respiratory profile. As illustrated in FIG. 4, the recorded turbulent exhale flow can be from the mouth (left), nose (center), and both nose and mouth simultaneously (right).

Dense Flow Reconstruction

Figure 5:
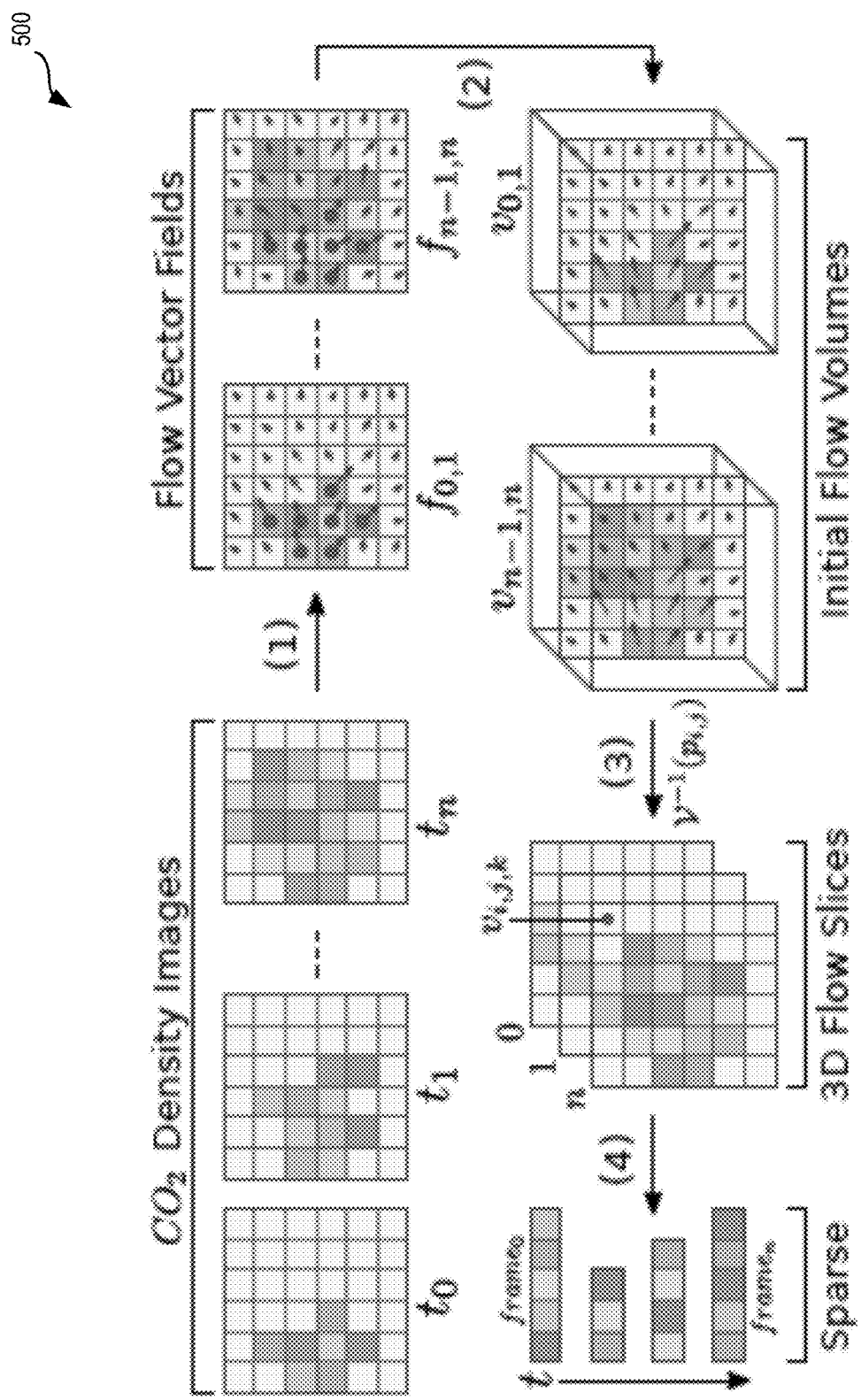
FIG. 5 illustrates various operations in an example of an exhale flow reconstruction process that approximates the reconstruction of the projected density volume by estimating the function density (x) using heuristic approximations in accordance with some embodiments of the present technology.

FIG. 5 illustrates various operations in an example of an exhale flow reconstruction process 500 that approximates the reconstruction of the projected density volume by estimating the function density (x) using heuristic approximations in accordance with some embodiments of the present technology. Dense flow reconstruction from two-dimensional imaging is inherently ambiguous and cannot be directly recovered. To approximate a resulting distribution of the flow within a reconstruction some embodiments employ a four step process for estimating exhale density flow behaviors based on consecutive $CO_2$ image pairs over time and space, outlined in FIG. 5.

In this process, various embodiments collect the set of n density images over time t, (1) compute the apparent flow through dense optical flow, (2) emplace these flow frames into a volumetric voxel grid as a seed slice in the middle of this volume, (3) extrapolate slice flow estimates, and (4) convert these scalar fields into sparse representations for each frame. The sparse representation is due to the dense resolution of the volumetric grid, which encodes the density value, and flow vector of each cell. Some embodiments evaluate each frame independently within this single compute volume. This results in an n frame recording, each composed of a sparse 3D scalar field that approximates disjoint flow behaviors recorded in each frame.

Figure 6:
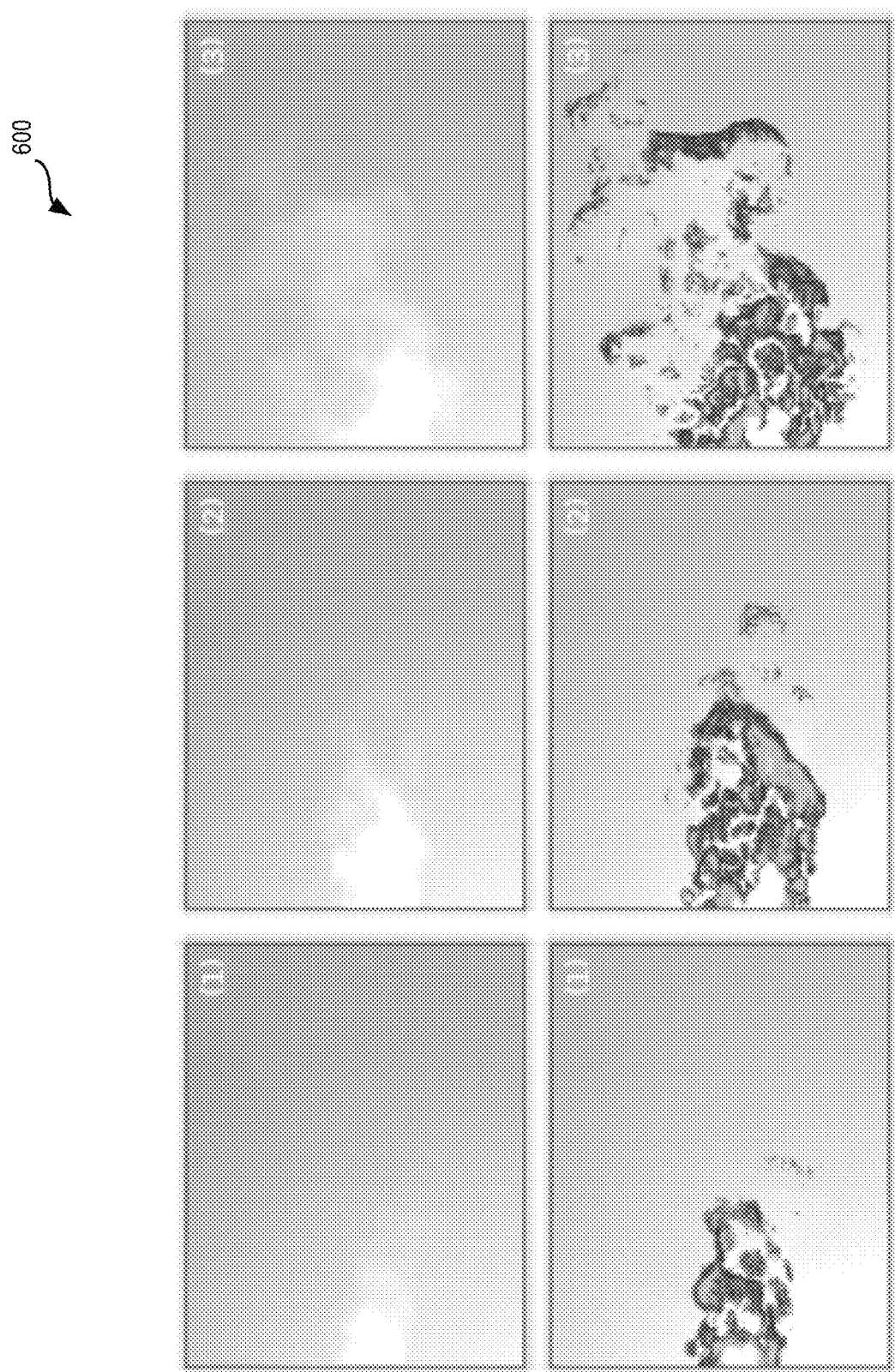
FIG. 6 illustrates an example of a set of turbulent exhale optical flow vectors where the generated vector field illustrates the apparent flow computed through a dense optical flow algorithm in accordance with various embodiments of the present technology.

FIG. 6 illustrates an example of a set of turbulent exhale optical flow vectors 600 where the generated vector field illustrates the apparent flow computed through a dense optical flow algorithm in accordance with various embodiments of the present technology. In the images illustrated in FIG. 6, the (top) row illustrates the original $CO_2$ density images, and the (bottom) row illustrates the resulting vector norm-color-mapped flow.

Experimental Results

Figure 7:
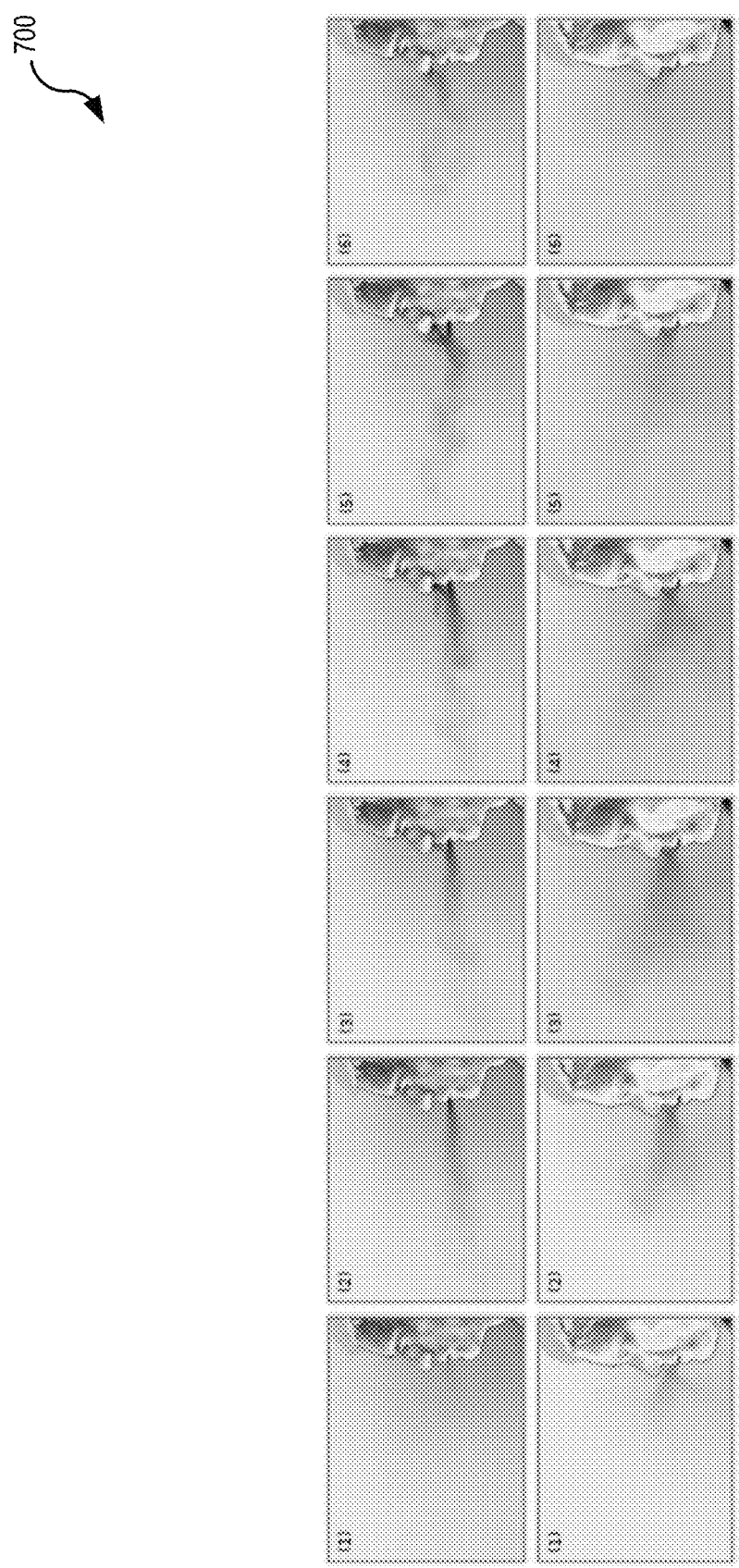
FIG. 7 illustrates a series of images showing the resulting $CO_2$ density distribution images illustrating unique respiratory patterns between individuals in accordance with various embodiments of the present technology.

The primary objective of flow-based respiratory analysis is to detect abnormalities within normal breathing based on the cross-sectional view of the exhale without the interference of background sources of infrared radiation. Since the objective of the reconstruction is to identify minute changes in the turbulent flow of an individual's exhale, some embodiments assume ideal posture and exhale region with a projection screen matte background. To focus the region to the exhale volume, our region of interest can be refined to exclude the face, but do not limit analysis to a region of interest. In FIG. 7 two six-frame segmented exhale flow sequences are presented. More specifically, FIG. 7 illustrates a series of images showing the resulting $CO_2$ density distribution images illustrating unique respiratory patterns between individuals in accordance with various embodiments of the present technology. For each image sequence, one exhale period has been recorded and visualized, showing the clear separation between the nose-mouth distribution and density flow behaviors. These flow behaviors unique to each individual are subject to their own physiology and can be evaluated to identify per-individual exhale traits.

Behavioral Analysis of Exhale Traits

Figure 8:
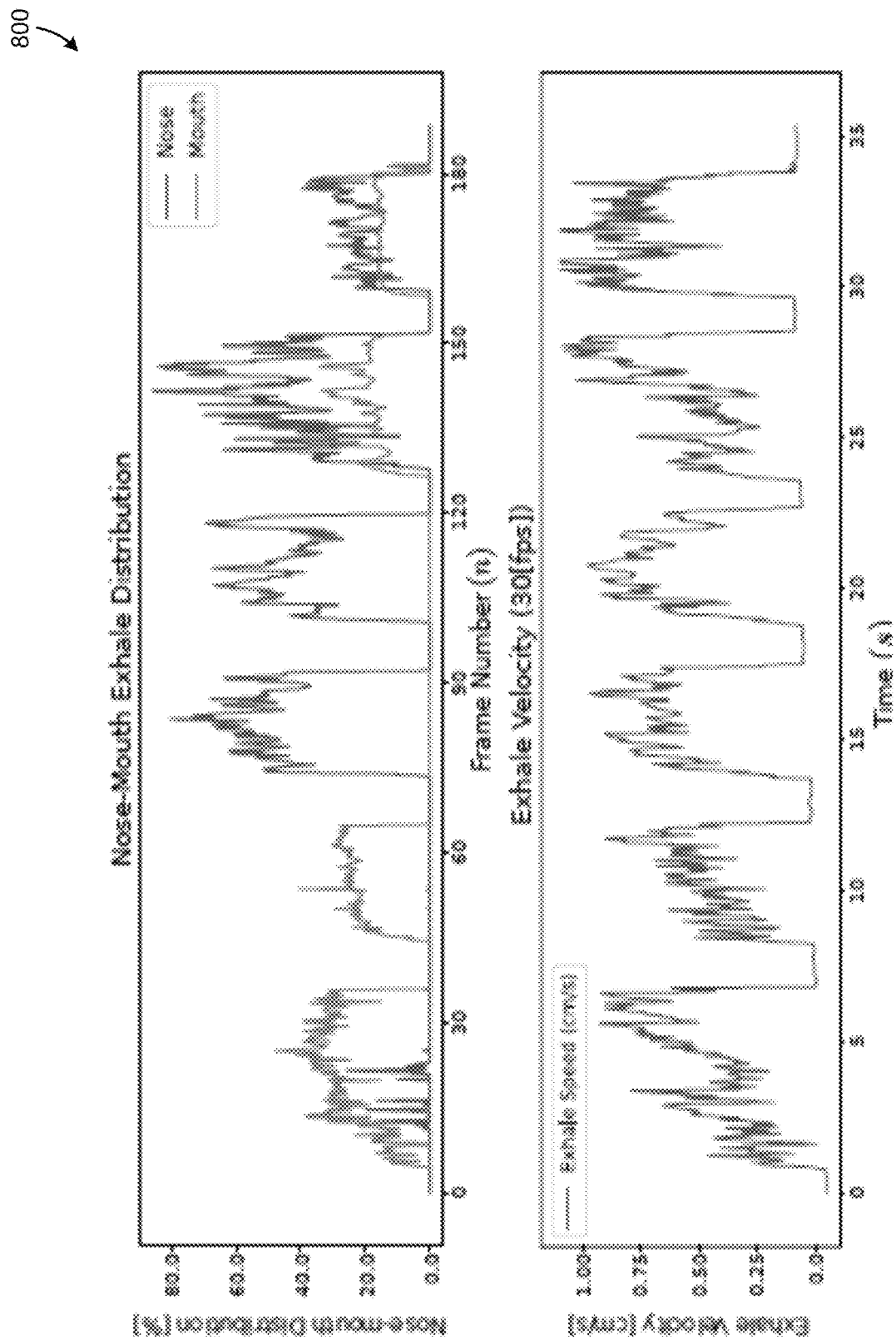
FIG. 8 illustrates plots of examples of the exhale nose-mouth distribution (top) for two exhales in each configuration: mouth, nose, and simultaneous oral-nasal breathing and the exhale velocity plot (bottom) demonstrates exhale characteristics for distance, strength, and the dissipation factor linked to $CO_2$ concentration in accordance with one or more embodiments of the present technology.

FIG. 8 illustrates plots of examples of the exhale nose-mouth distribution (top) for two exhales in each configuration: mouth, nose, and simultaneous oral-nasal breathing and the exhale velocity plot (bottom) demonstrates exhale characteristics for distance, strength, and the dissipation factor linked to $CO_2$ concentration in accordance with one or more embodiments of the present technology.

Figure 9:
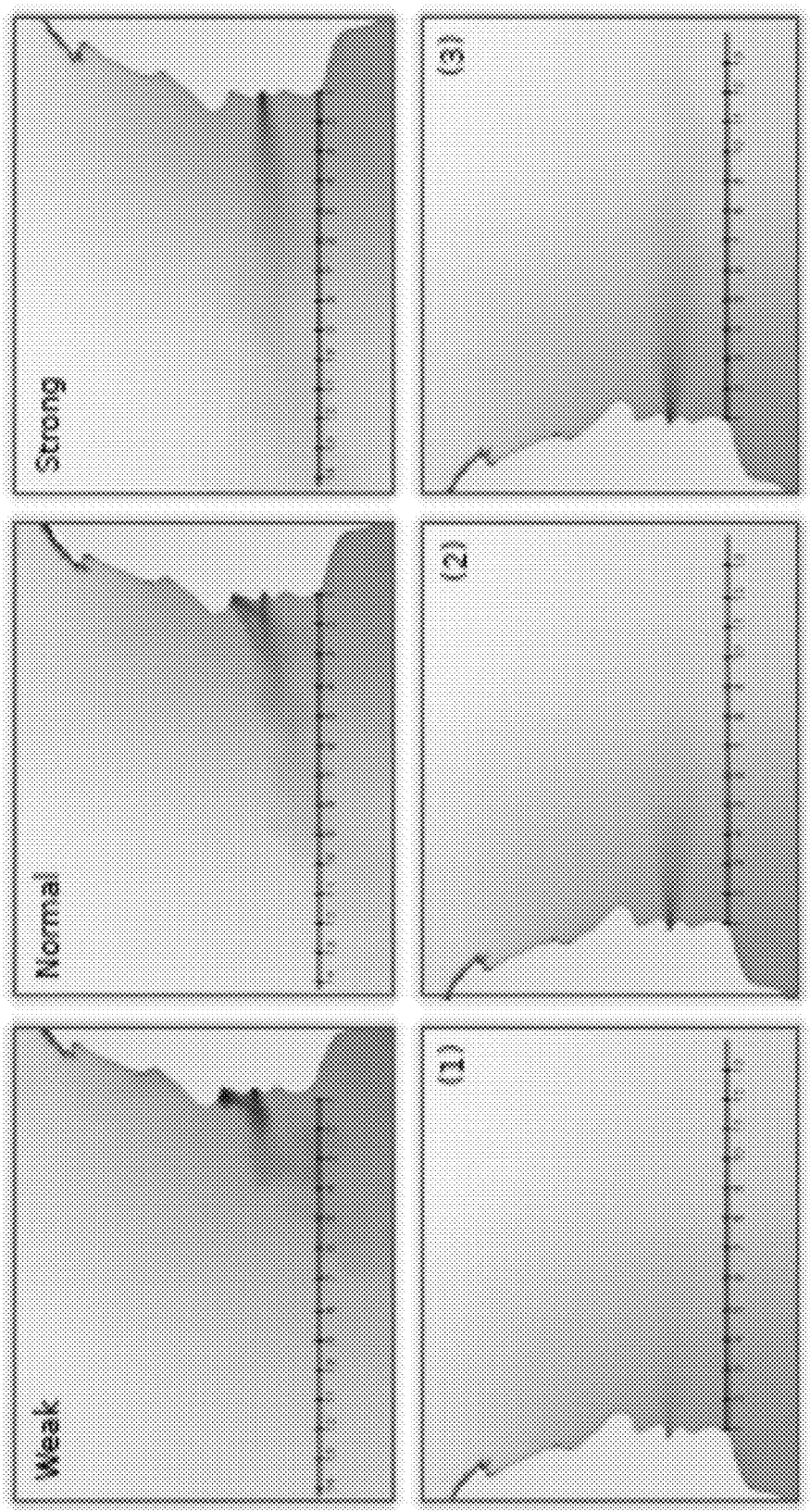
FIG. 9 illustrates an example of resulting videos for weak, normal, and strong exhale strengths (top row) and exhale velocity differentiated per frame for slow, normal, and fast velocities (bottom row), as a function of the exhale speed, $CO_2$ concentration, and the environmental thermal dissipation rate in accordance with various embodiments of the present technology.

The results of the proposed method present both flow visualization and approximated volumetric flow reconstruction to evaluate exhale strength and velocity shown in FIG. 9 nose-mouth distribution, strength, and minute flow variances that can be associated with differentiating between normal and abnormal breathing. These contributions will greatly broaden the horizon of exhale analysis over existing frequency-based methods that utilize Fourier transforms to directly compute breathing rate.

Quantitatively, the relative nose-mouth distribution can be expressed as an estimated contribution to the exhale. For the velocity component, the change in exhale length over time can be expressed as a result of exhaled $CO_2$ concentration.

Flow Reconstruction

Figure 10:
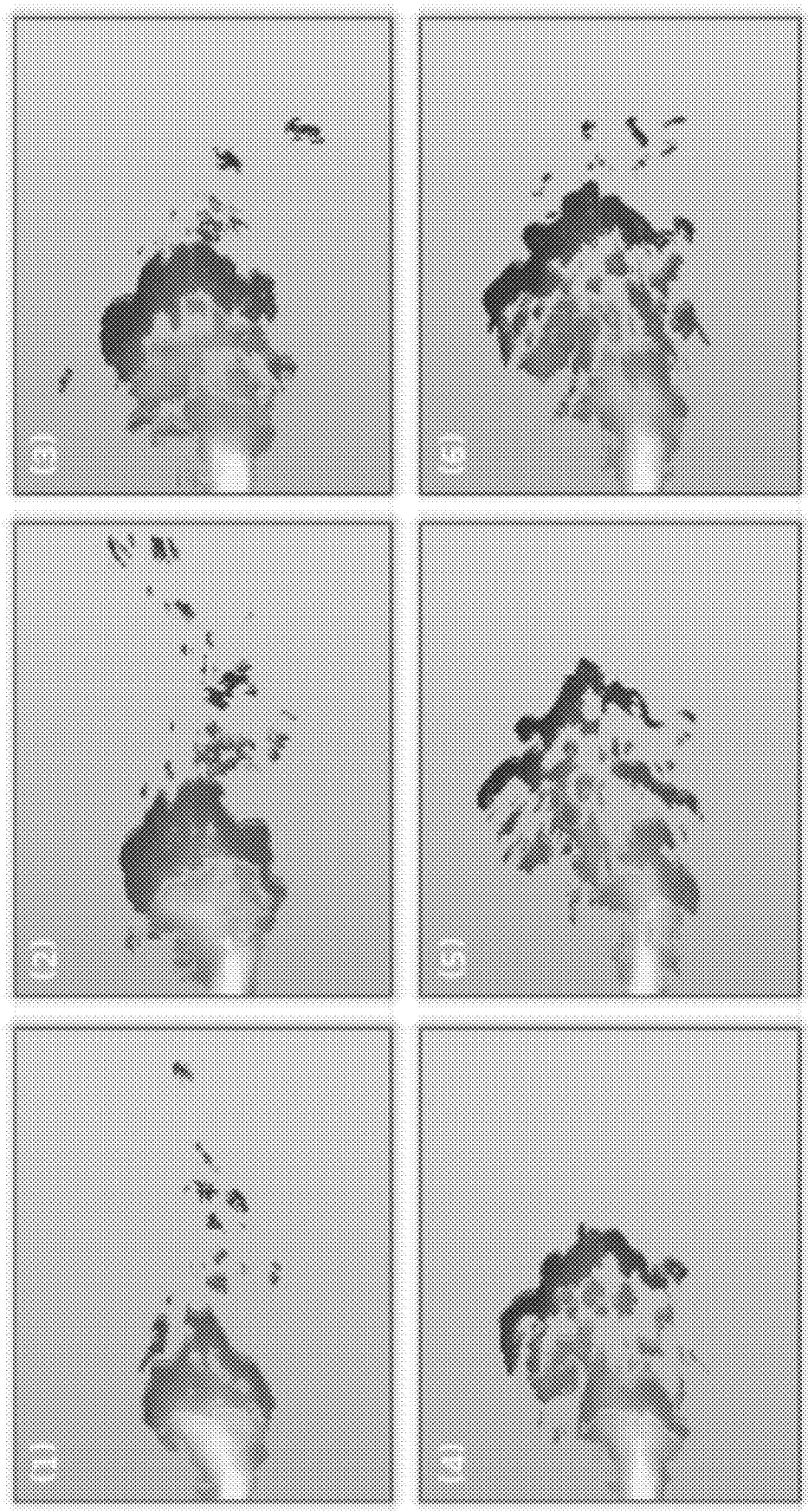
FIG. 10 shows a reconstructed 3D sparse exhale flow sequence rendered as a color-mapped sparse cloud (from top-left to bottom-right) incorporating interchangeable heuristics for extrapolating 3D flow fields in accordance with various embodiments of the present technology.

The extrapolation of our flow analysis into our 3D sparse scalar field is defined by the application of spatial filters that define 3D kernel flow behaviors in three-dimensional space starting from known quantitative estimates of flow behavior. This cleanly separates the exhale densities from the residual general interference from background sources and natural environmental airflow. Using this technique, some embodiments can completely reconstruct segmented exhale behaviors. The resulting reconstruction is rendered as volumetric clouds within FIG. 10.

Evaluation and Discussion

Turbulent flow analysis is inherently complex. Differentiating intersecting flows projected onto a two-dimensional image plane further complicates the analysis for natural nose/mouth separation and breathing metric extraction. Accurate 3D reconstruction of volumetric flows without depth measurements or advection is also intangible. To preserve validity of our model, some embodiments focus on maintaining flow behavior characteristics, but do not formulate an exact volumetric exhale reconstruction. Rather, this form of exhale imaging opens up a new medical significance in the monitoring of normal versus pathological airflow from the lower and upper airways. Volume measurements quantify lung capacity or effect of therapy in pulmonary patients with common medical problems such as asthma and chronic obstructive pulmonary disease without the need to utilize bulky pulmonary function machines with required patient cooperation which subject's measurements to effort-related errors. Subtle alterations of airflow velocity and nose-mouth distribution is a plausible method to determine upper airway obstruction or those at risk for sleep apnea or sudden infant death syndrome. With the ability to monitor subtle changes in airflow in infants sleeping prone versus supine or in car seats or soft bedding, the advancement of research into the cause and prevention of SIDS cases achieves a new trajectory in high-resolution $CO_2$ respiratory behavioral analysis.

Estimation Techniques

Figure 11:
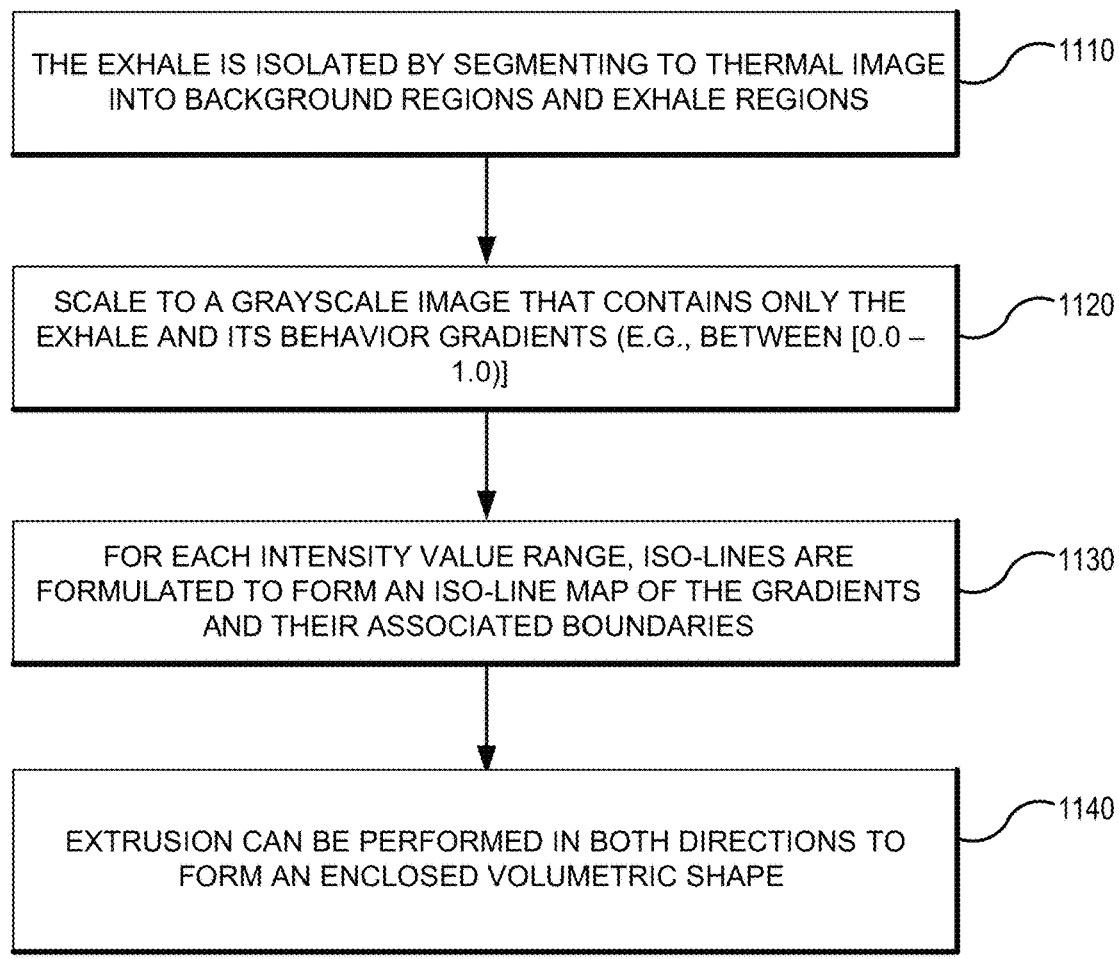
FIG. 11 is a flowchart illustrating an example of a set of operations that represent the exhale volume within a closed surface representing a region that encloses all of the visible $CO_2$ gas that may be used in one or more embodiments of the present technology.

FIG. 11 is a flowchart illustrating an example of a set of operations 1100 that represent the exhale volume within a closed surface that represents the region that encloses all of the visible $CO_2$ gas that may be used in one or more embodiments of the present technology. As illustrated in the embodiments shown in FIG. 11, isolation operation 1110 can isolate the exhale flow through identifying exhale fluid flow behaviors that segments the exhale from the background of the thermal image from the exhale regions. This is obtained through the process of identifying shifts within the intensity values within the image to construct a flow-field of velocity vectors. This vectors represent an approximation of the apparent flow illustrated in the image over a small increment in time. This segmentation can be obtained by characterizing the exhale flow behavior through its unique fluid movement estimated by using a parallel form of optical flow.

Fluid velocity vectors obtained between discrete times can then provided to a pixel classification model to identify exhale pixels within the image and isolate them from background pixels. For example, in some embodiments, isolation operation may assume an approximate time between subsequent image frames as dt and implement some version of the following:

(0) Input: Thermal image sequence $I_T(t_0), \ldots, I_T(t_0 + n * dt)\ \forall n \in S$, for image sequence S
  with length n collected over time interval (n * dt) starting at $t_0$
(1) Acquire thermal (T) image $I_T(t)$ at time t and next in sequence image $I_T(t + dt)$
(2) Generate spatial derivative image $I_x = (d/dx)$ and $I_y = (d/dy)$ numerically
(parallel)
(3) Generate temporal derivative image $I_t = I_T(t + dt) - I_T(t)$ between subsequent images
(4) Until convergence, refine velocity vectors to generate 2D velocity field $V_I$
  Estimate velocity vector $\vec{v}_{i,j}$ for each pixel $p_{i,j}$ for $V_I(i, j)$
  Refine estimation of $\vec{v}_{i,j}$ forming fluid motion relative to each pixel
(5) For each pixel $p_{i,j} \in I$: Classify apparent flow behavior contributing to fluid
  motion using $V_I(i,j)$:
  Apply (n × n) classification filter to pixel at index i, j
  For pixel $p_{i,j}$ assign label $l \in$ {exhale flow, background, movement, other}
(6) Output: Label image containing labels for each pixel $p_{i,j} \in I_T(t)$ The application of the labeled output image provided by isolation operation 1110 for each image within the provided sequence may generate a set of images that contain labeled pixels where each image contains the isolated exhale intensity distribution separated from background sources of infrared. Temperature scaling operation 1120 can generate a grayscale image that contains only the exhale and its behavior gradients. For example, in some embodiments, temperature scaling operation 1120, given a collection of exhale isolated thermal images at time interval dt, may implement some version of the following:

(0) Input: Segmented thermal image sequence $s_T(t_0), \ldots, s_T(t_0 + n * dt)\ \forall n \in S$, for
  sequence S of length n collected over time interval (n * dt) starting at $t_0$
(1) Obtain the min ($p_{min}$) and max ($p_{max}$) pixel intensity values within exhale
region
(2) For each pixel $p_{i,j} \in S_T(t)$:
  Scale $p_{i,j}$ relationally to its intensity and fluid velocity vector $\vec{v}_{i,j}$
(3) Output: Combined data aggregate containing pixel image intensity $p_{i,j}$ for all
  pixels with associated velocity vector $\vec{v}_{i,j}$ and segmentation label l Mapping operation 1130 can generate iso-lines (creating an iso-line map) of the gradients and their associated boundaries to create a one-sided representation of the volume. The computed data aggregate contains captured thermal $CO_2$ signature signal strength in addition to the estimated apparent velocity associated with each pixel between subsequent frames. From the labels associated with each pixel in the aggregate, the flow behavior of the exhale can be identified. Within this subset of exhale labeled pixels, volume characteristics are estimated using the intensity and flow velocity vectors. For each intensity value range, iso-lines can be formulated orthogonal to the direction of the velocity vectors to generate an iso-line map of the gradients and the associated boundaries of the exhale for all intensity values.

This map describes the dissipation direction of the exhale through the sequence of captured images. Based on symmetric approximation, or asymmetric reconstruction through observation of apparent flow behaviors, extrapolation operation 1140 can be performed in multiple directions to form an enclosed volumetric shape that represents the exhale volume represented in the computed data aggregate that describes the apparent flow of the CO2 exhale. Based on the output of 1130, the metric units of the volume are defined by identifying pixels within the depth image that corresponds to the timestamp of the collected thermal image.

The metric unit that describes the spatial measurement between pixels within the depth image are used to identify the spatial relationship between adjacent pixels within the thermal image. This spatial information is then provided to the flow data aggregate to define the real-world scale of the exhale. In some embodiments, extrapolation operation 1140, given the data aggregate from the output of 1130, can perform some variation of the following:

(1) Input: Exhale data aggregate for each frame that contains per-pixel
information:
  {intensity, velocity, label, flow features}
(2) Generate a 3D voxel grid $v_{i,j,k}$ with sufficient size to represent the exhale or
up-sampled form of the input data aggregate
(3) Seed the center slice of the voxel grid using the input data aggregate
(4) For each voxel $v_{i,j,k}$ within the discrete reconstruction volume:
  Extrapolate relative density to neighboring voxels based on seed slice
  diffusion factor, velocity $v_{i,j}$, and flow features
(5) Output: 3D Voxel representation of the exhale flow approximated by an inverse
  volumetric construction.

Figure 12:
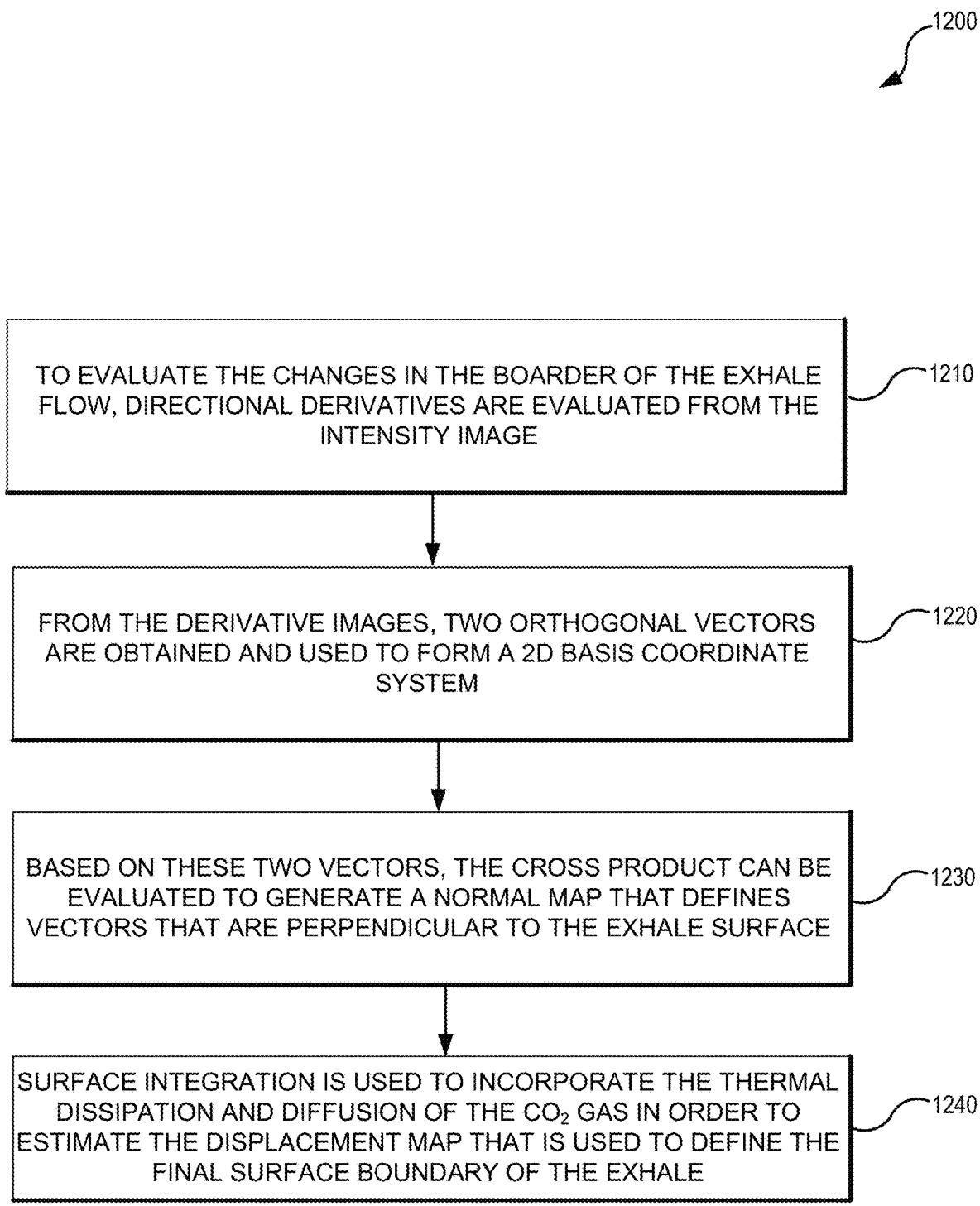
FIG. 12 is a flowchart illustrating an example of a set of operations for generating an exhale shape from $CO_2$ intensity shading that may be used in one or more embodiments of the present technology.

FIG. 12 is a flowchart illustrating an example of a set of operations 1200 for generating an exhale shape from $CO_2$ intensity shading that may be used in one or more embodiments of the present technology. In accordance with various embodiments, the output of this process is a dense representation of the flow volume exhibited by the input exhale data aggregate corresponding to the sub-region of the image that contains the exhale flow behavior. From this dense cluster of 3D voxel information, extrusion of the initial slice (2D image) used to generate the approximation can then used to extract an enclosed volumetric shape that provides an approximate estimate of the exhale volume. Each voxel within this representation may contain an estimate of the estimated $CO_2$ density as a function of the detected pixel intensity from the input data aggregate placed into the center of the 3D volumetric cube that contains all voxels. The voxels used in the initial seeding (center slice of the voxel cube) can then be propagated outward from the slice to form a volumetric shape that approximates the apparent exhale flow region in 3D space.

In accordance with various embodiments, thermal images may contain an intensity-based $CO_2$ distribution describe a static state of the exhale flow captured by each frame that can be modeled as a three-dimensional surface enclosing the exhale volume. A segmented image is defined as a set of gradients that are defined by the $CO_2$ gas, but used to define the curvature of the gas as it flows. In the embodiments shown in FIG. 12, to evaluate the changes in the border of the exhale flow, computation operation 1210 evaluates directional derivatives from the intensity image. This includes a Finite Differences (FD), Sobel, or other approximations of the (dx), and (dy) derivatives of the image. From the derivative images, basis operation 1220 identifies two orthogonal vectors and uses the tow orthogonal vectors to form a 2D basis coordinate system. Based on these two vectors, the cross product can be evaluated during evaluation operation 1230 to generate a normal map that defines vectors that are perpendicular to the exhale surface.

In accordance with various embodiments, operation 1210-1230: Detecting exhale border from estimated directional flow vectors over time can be implemented using some version of the following:'

(1) Input: A collection of voxel grids $V(t_i)$ in 3D space defining a 3D Voxel reconstruction of the flow volume corresponding to each frame at time index $t_i$ for a total of n collected frames. Each voxel includes: intensity, velocity, label, flow features for all voxels included in the 3D approximation
(2) For each voxel $v_{i,j,k}$:
   Identify border voxels that represent the boundary between the enclose exhale
   volume and the surrounding environment
(3) For each of these voxels on the boundary evaluate surface normals of
the enclosed region of the exhale based on the directional derivatives
of the surface evaluated from the voxel structure
(4) Output: A voxel grid $V(t_i)$ for each captured frame at time-step $t_i$ that contains
border voxel labels and surface normals that correspond to apparent flow directions
of the exhale.

Surface integration operation 1240 can incorporate the thermal dissipation and diffusion of the $CO_2$ gas in order to estimate the displacement map that is used to define the final surface boundary of the exhale. In the instance where the voxel grid reconstruction method is not used, a symmetric model can be extrapolated from the exhale flow image data aggregate of 1220. In some embodiments, the pixel labels, flow direction and derivatives can be generated using operations 1210, 1220, and 1230. This results in a dense set of surface normals that describe the surface of the exhale from a two-dimensional image. Since this image is flat and provides surface normals for each pixel, the image composes a normal map. The normal map stores the estimated surface normals of the exhale for each pixel. From the normal map, displacements can be generated to from a displacement map.

The displacement map can be generated using numerical integration of the underlying surface normals to approximate the surface that satisfies the following constraint: the normal of each pixel is perpendicular to the surface defined by the displacement map. Therefore, connecting a grid mesh across the displacement map will create a discrete surface representation where at each pixel, the surface will be defined such that it will be perpendicular to the provided normal map. For example, operation 1240 can provide for the generation of a symmetric exhale model. In various embodiments, this can be implemented as a variant of the following:

(1) Input: Exhale data aggregate image containing directional derivative
vector sand the normal vectors $\hat{n}_{i,j}$ for each pixel $p_{i,j}$
(2) Generate a displacement map used to approximate the surface
height of the exhale to reconstruct half of the enclosed exhale volume,
all heights are initially zero
(3) For each pixel $d_{i,j}$ in the displacement map:
   Generate a height that satisfies constraint: $\hat{n}$ is orthogonal to displaced
height
   for all neighboring normals, assuming the height represents discrete
   samples of the continuous underlying surface
(4) Output: Generate a surface mesh connecting all displacement pixels
$d_{i,j}$ into a regular grid that approximates the surface described by the
provided normal map. This surface is then mirrored about the image
plane to construct an approximate 3D shape of the enclosed exhale
region.

Figure 13:
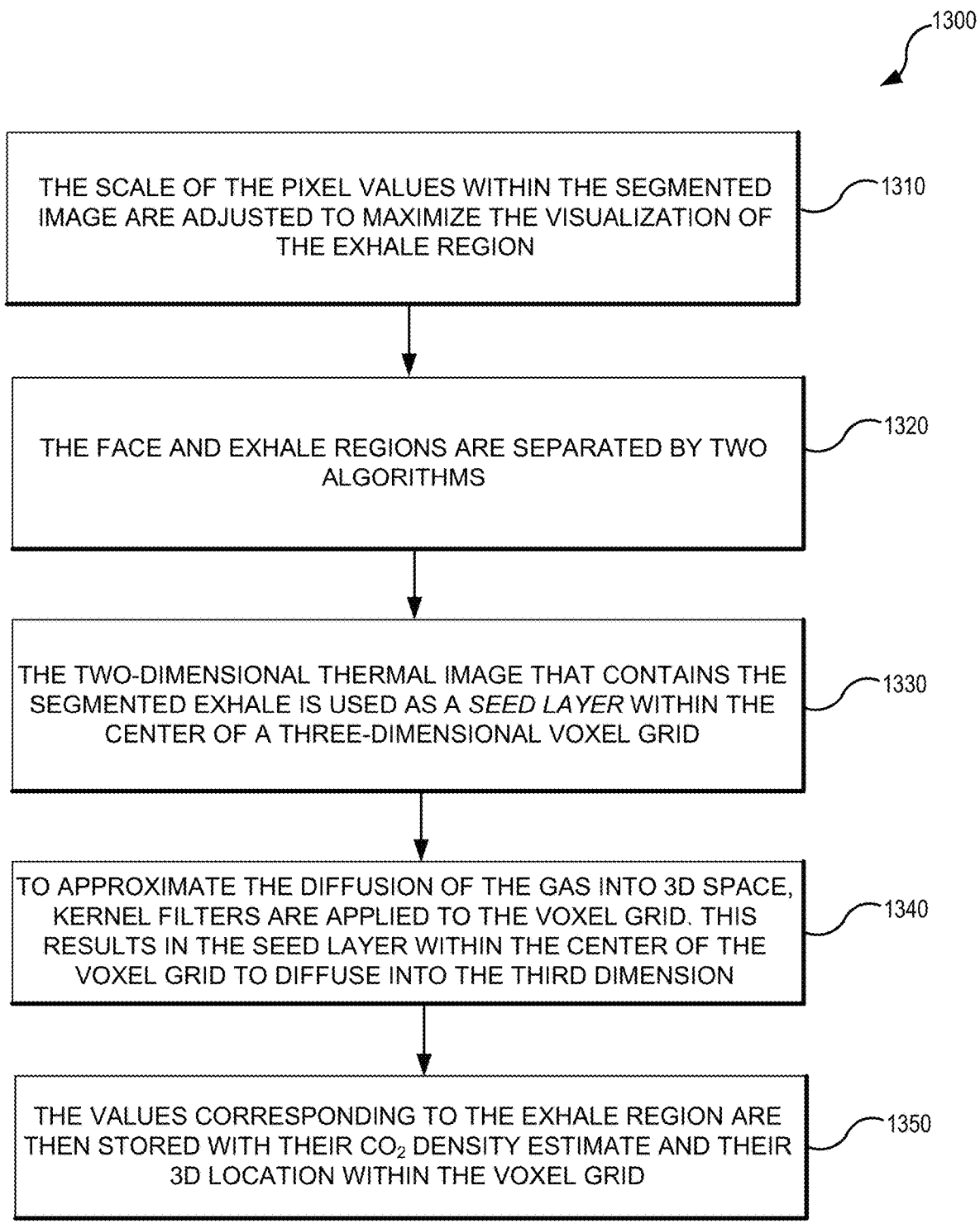
FIG. 13 is a flowchart illustrating an example of a set of operations for sparse voxel reconstruction that may be used in one or more embodiments of the present technology.

FIG. 13 is a flowchart illustrating an example of a set of operations 1300 for sparse voxel reconstruction that may be used in one or more embodiments of the present technology. The objective of this technique is to eliminate the notion of a hard-boundary method for representing exhale volumes. As defining a hard arbitrary boundary may introduce error within the estimated volume, fuzzy boundaries are introduced to provide a smooth transitions between the identified enclosed volume and the surround environment.

As illustrated in FIG. 13, scaling operation 1310 adjusts the scale of the pixel values within the segmented image to maximize the visualization of the exhale region. In accordance with various embodiments, scaling operation 1310, can include obtaining infrared sensed thermal values for by segmentation for maximizing signal entropy within the exhale region. This may be implemented in some embodiments using the following or a variant thereof:

(1) Input: Image containing thermal exhale pixel intensities and flow estimated velocity vectors that describe apparent fluid flow
(2) For all estimated flow vectors within the image, identify those that describe the exhale flow sub region of the image
(3) Within this region, identify the pixels with the minimum and maximum intensity values that explicitly belong to the exhale flow
(4) Perform a scaling of the image values based on the minimum and maximum values identified in (3) to maximize the entropy of the exhale flow within the image
(5) Output: Image of scaled thermal values that maximize entropy of the exhale behavior within the segmented exhale sub-region of the input image Segmentation operation 1320 separates the face and exhale regions. In accordance with various embodiments, this can be done by (1) temperature or thermal pixel intensity segmentation to eliminate a subject's face, body, or background heat sources from the image, and/or (2) dense optical flow between frames to identify changes over time and extract regions with high flow values.

Seeding operation 1330 identifies the two-dimensional thermal image that contains the segmented exhale and uses this image as a seed layer within the center of a three-dimensional voxel grid (x,y,z). Diffusion operation 1340 approximates the diffusion of the gas into 3D space. This diffusion process is modeled using kernel filters can be applied to the voxel grid. There may be multiple variations of the kernels that are used to approximate the diffusion process illustrated by the recorded image sequence.

The seed layer within the center of the voxel grid is used as the initial estimate of the gas distribution through the discretized volume. The diffuse kernels are applied to the voxel grid starting at the seed layer to define an embedding of the flow behavior into the third dimension, approximating a 3D reconstruction of the observed behavior. This method utilizes approximate flow estimation vectors as part of a dense flow estimate to impose space-time constrains on the potential flow behaviors reconstructed in 3D space. Sparse representation operation 1350 takes the values corresponding to the exhale region and store the values with their $CO_2$ density estimate and their 3D location within the voxel grid. The outcome is a discrete 3D representation of the exhale flow behavior within the voxel grid.

Figure 14:
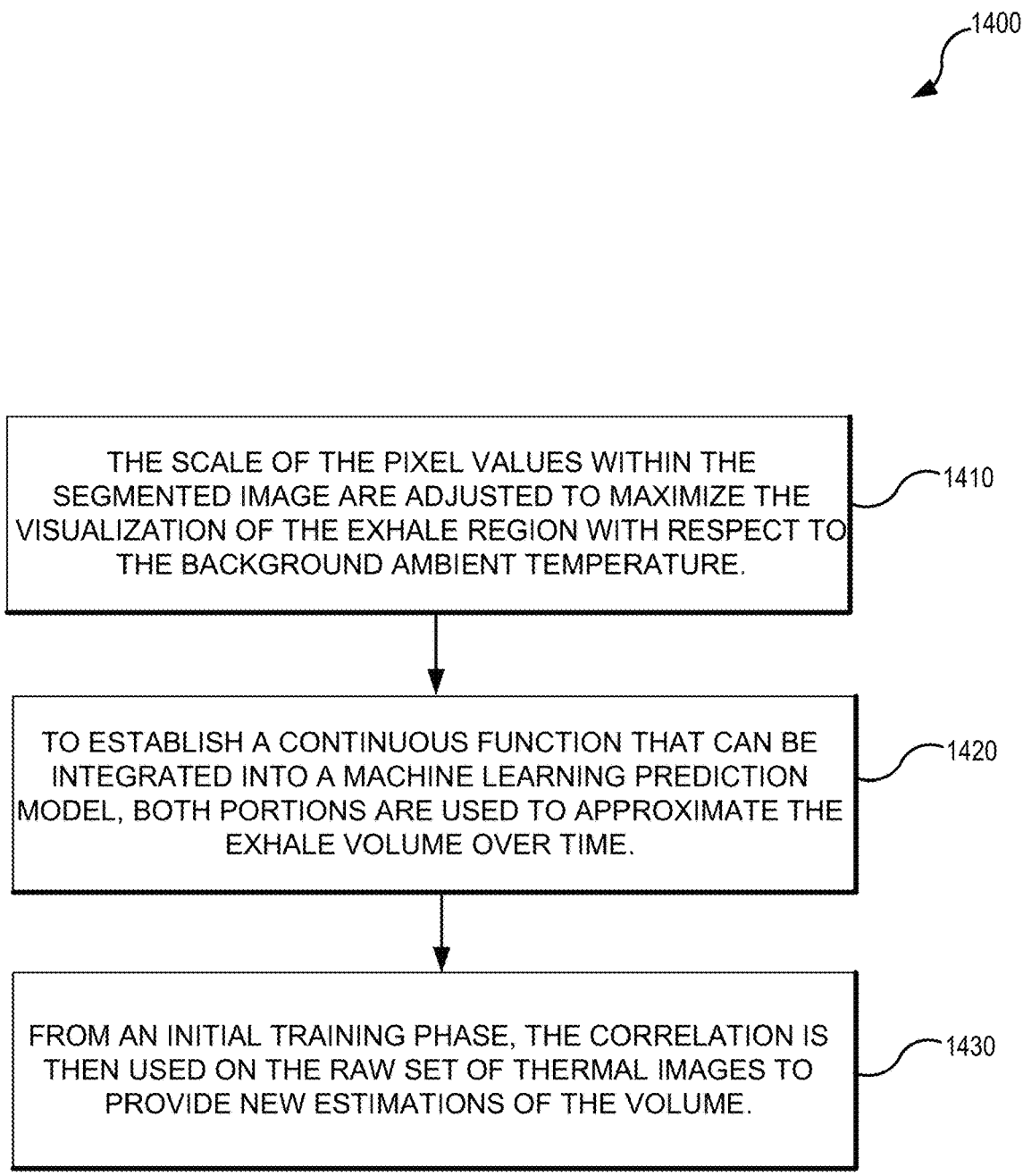
FIG. 14 is a flowchart illustrating an example of a set of operations for correlating volume estimation through machine learning that may be used in one or more embodiments of the present technology.

In operations, 1330-1340, voxel grid exhale volumetric reconstruction can be performed using the following or a variant thereof:

(1) Input: A collection of image frames F collected over time using a sampling rate dt that contain intensity and flow data as an input image I
(2) Generate a voxel grid of dimensions width, height, depth sufficient for holding the input image defined by its image width and height which will be placed at depth/2
(3) Copy the input image to the center of the voxel grid, this defines a single slice of voxels within the grid will obtain the values from the input image (intensity, velocity estimates, labels, and flow features)
(4) For each voxel $v_{i,j,k}$ within the slice layer, the initial $p_{i,j}$ intensity and flow velocity estimate $\vec{v}_{i,j}$ corresponding to each pixel of the slice layer is used as a seed to begin the diffusion process enabled by applying the volumetric kernels to the voxel grid
(5) For each voxel $v_{i,j,k}$ within the remaining cells of the voxel grid outside of the slice layer, evaluate a selected diffusion kernel to extrapolate the flow from the seed layer to fill the surrounding voxels
(6) Output: Voxel grid with a discrete 3D approximation of the exhale behavior for each collected image frame. The number of output voxel grids is equal to or greater than the number of input image frames F FIG. 14 is a flowchart illustrating an example of a set of operations 1400 for correlating volume estimation through machine learning that may be used in one or more embodiments of the present technology. Some embodiments of the present technology obtain a volume estimate by establishing a behavioral correlation between the exhale flow obtained from processing a thermal image and a ground-truth (or gold standard) value obtained using a traditional or industry standard device. Various embodiments of this technique assume that there the subject's face is visible within the devices field of view.

Scaling operation 1410 adjusts the scale of the pixel values within the segmented image to maximize the visualization of the exhale region with respect to the background ambient temperature. Approximation operation 1420, approximates the exhale volume over time to establish a continuous function that can be integrated into a machine learning prediction model. From an initial training phase, estimation operation 1430 uses the correlation on the raw set of thermal images to provide new estimations of the volume.

Figure 15:
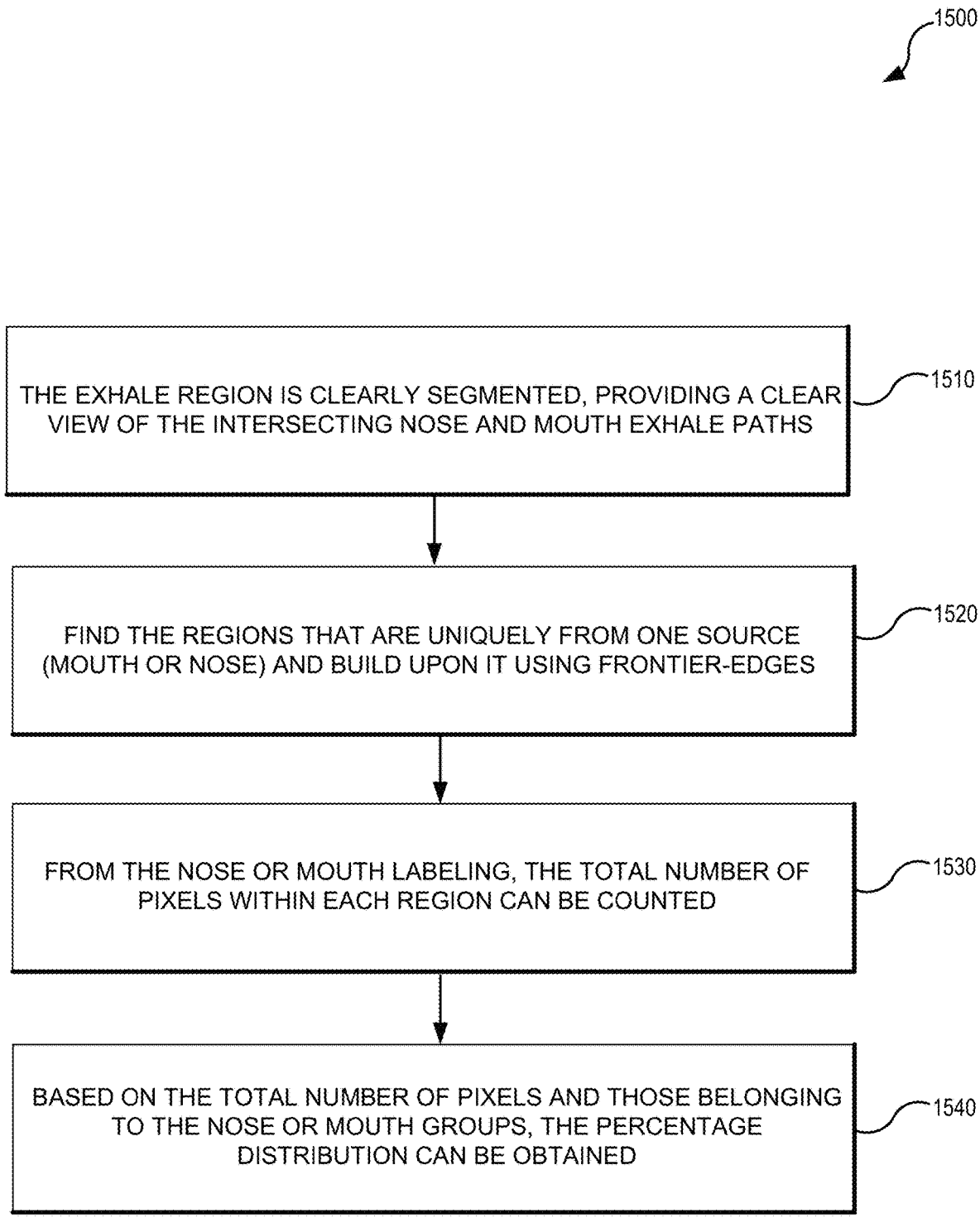
FIG. 15 is a flowchart illustrating an example of a set of operations for establishing which portion of the exhale volume is from the nose or mouth during continuous breathing that may be used in one or more embodiments of the present technology.

FIG. 15 is a flowchart illustrating an example of a set of operations 1500 to establish which portion of the exhale volume is from the nose or mouth during continuous breathing that may be used in one or more embodiments of the present technology. Various embodiments of this technique assume a perpendicular view of the patient's face is available. The face is the hottest focal content of the image and the background is thermally uniform and cooler than the face temperatures As illustrated in FIG. 15, segmentation operation 1510 segments the exhale region to provide a clear view of the intersecting nose and mouth exhale paths. Analysis operation 1520 identifies the regions that are uniquely from one source (mouth or nose) and build upon it using frontier-edges. This will allow the system to isolate the sections of the image that belong to the mouth or nose exhale, allowing each pixel to be labeled none, nose, or mouth. This method can also be extended to identify the flow from each nostril of the nose. In this instance, the labels include: none, nostril-left, nostril-right, or mouth. From the nose or mouth labeling, the total number of pixels within each region can be counted during counting operation 1530. Based on the total number of pixels and those belonging to the nose or mouth groups, the percentage distribution can be obtained during distribution operation 1540.

Figure 16:
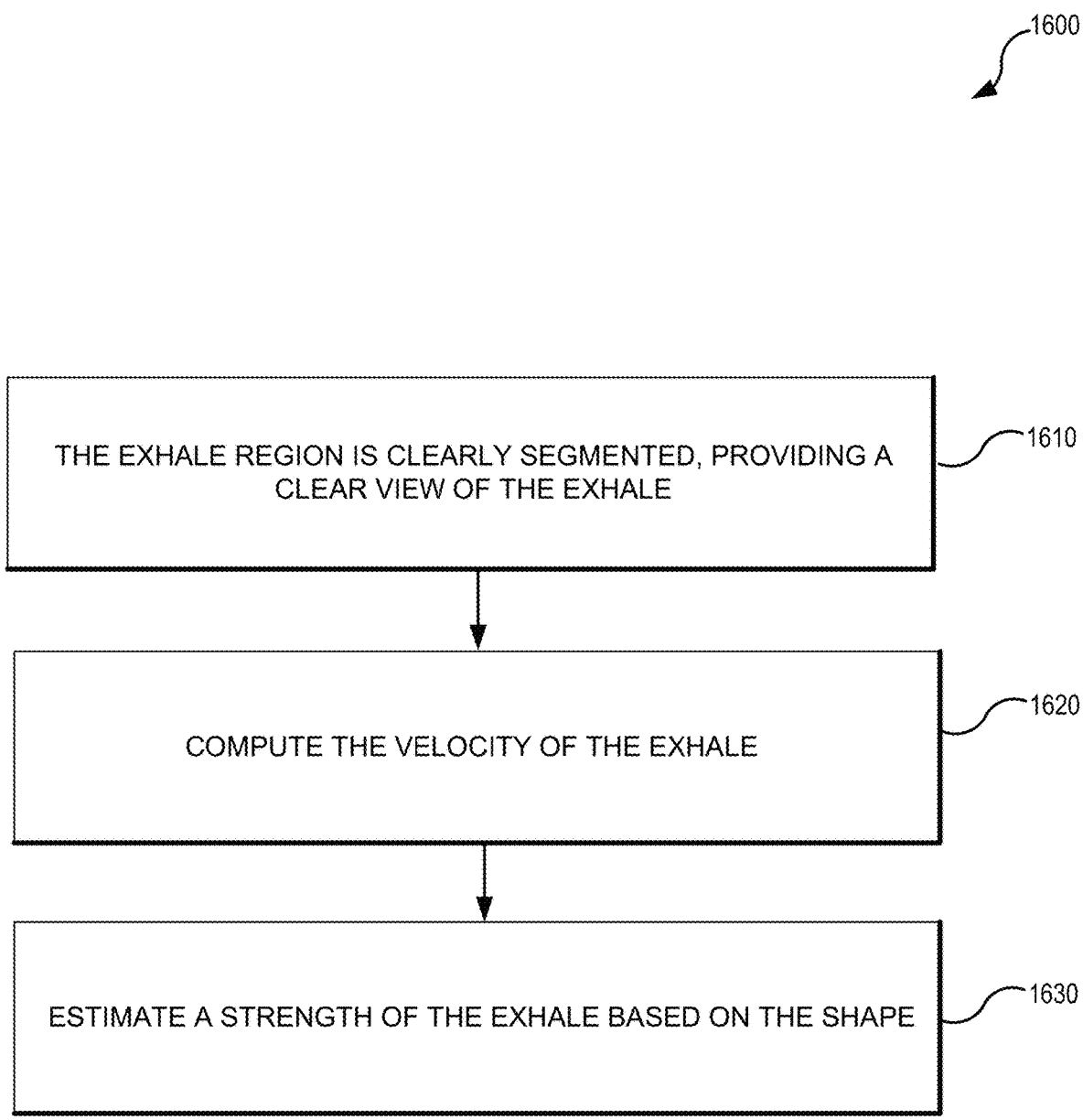
FIG. 16 is a flowchart illustrating an example of a set of operations for evaluation of breathing strength evaluated as a function of velocity, volumetric distribution, and flow behavior that may be used in one or more embodiments of the present technology.

FIG. 16 is a flowchart illustrating an example of a set of operations 1600 for evaluation of breathing strength. Breathing strength is evaluated as a function of velocity, volumetric distribution, and flow behavior that may be used in one or more embodiments of the present technology. One benefit of embodiment embodiments of this technique is that the quantitative evaluation of breathing strength can be evaluated as a function of velocity, volumetric distribution, and flow behavior. Various embodiments of this technique assume a perspective camera view where the subject's face is visible within the device defined viewing angle.

As illustrated in FIG. 16, segmentation operation 1610 segments the exhale region providing a clear view of the exhale. The velocity of the exhale is computed during estimation operation 1620. In some embodiments, the velocity can be composed of two primary factors: (1) measuring the differences between frames obtained at a fixed interval providing the timing required to evaluate velocity, and (2) the distance measurements obtained using the depth image that are correlated with estimated velocities to provide metric units. Using an approximation of the exhaled volume, the shape of this volume can be used by estimation operation 1630 to estimate or classify the strength of the exhale.

Figure 17:
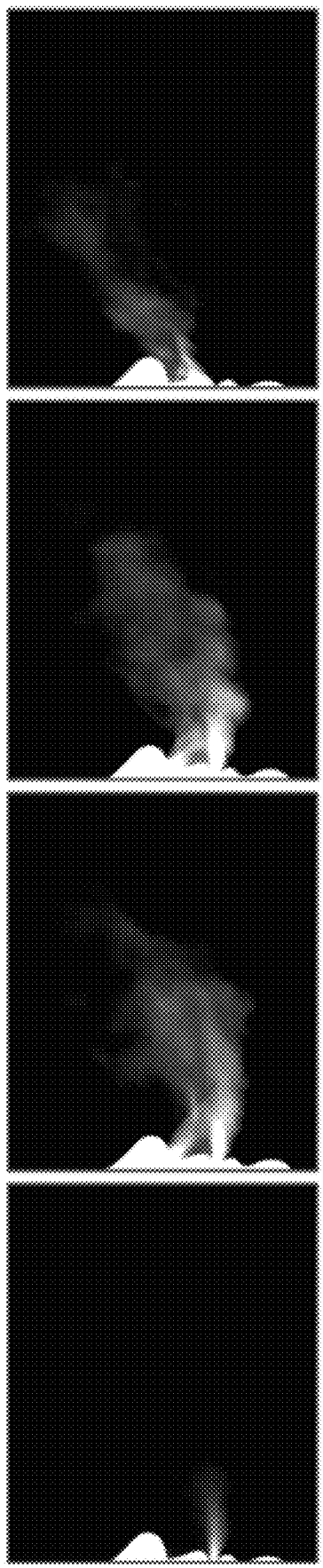
FIG. 17 is a high contrast thermal imaging of the exhale $CO_2$ distribution using various embodiments of the present technology.

FIG. 17 is a high contrast thermal imaging of the exhale $CO_2$ distribution using various embodiments of the present technology. The image sequence represents the progression of the heat dissipation and $CO_2$ diffusion as it mixes with the surrounding environment. The image value scale range is optimized to visualize the exhale thermal values, resulting in a loss of facial detail but providing a clear picture of the exhale. To provide the first steps towards creating a new set of quantitative respiratory metrics that represent natural breathing, some embodiments introduce a set of new metrics that can be obtained through analyzing turbulent exhale behaviors that are visible using $CO_2$ exhale imaging. Based on this work, some embodiments are capable of obtaining high-contrast thermal exhale images that can be used for detailed behavioral analysis (FIG. 17). This includes the addition of turbulent flow analysis using dense optical flow, nose to mouth distribution, strength, velocity, and a sparse 3D reconstruction of exhale sequences.

Figure 18:
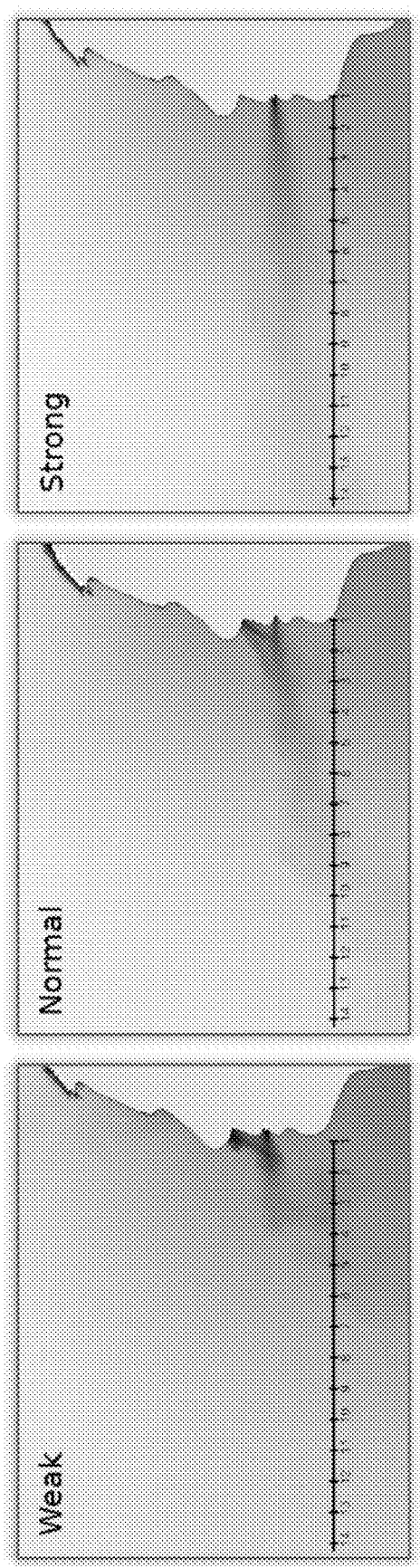
FIG. 18 illustrates an example of the changes in the exhale flow depending on strength, where the strength evaluation is a function of the velocity and flow behavior which can vary drastically from weak exhales (left) to strong exhales (right), that may be used in various embodiments of the present technology.

Individualized respiratory behaviors also contribute to how some embodiments can analyze the patient-specific pulmonary conditions. Over time, every individual has a fluctuation in their natural breathing behavior both between mouth breathing and the distribution between nostrils. These behaviors can fluctuate during the day and provide insight into the current state of a patient's respiratory heath. The image sequences in FIG. 18 illustrate the differences that can be identified between the exhale flows of different individuals. The result of this analysis allows us to provide a deeper understanding of how a per-patient exhale model can be established for long term monitoring and condition changes.

Prior methods that utilize $CO_2$ imaging rely on the use of an ideal viewing angle. In many of the prior systems, it is assumed that the viewing angle is perfectly perpendicular to the direction of the exhale. This works well for experimental setups and allows for numerous metrics to be collected. However, this assumption is extremely rigid and limits the applicability of this approach. Therefore, to provide a feasible monitoring solution that can be clinically deployed, some embodiments introduce a new set of algorithms that can be used with any orientation, even those that will introduce complex background interference such as the patient's face, other monitoring equipment, or general environmental heat sources that can obscure the thermal signature of the $CO_2$ that represents an exhale.

Figure 19:
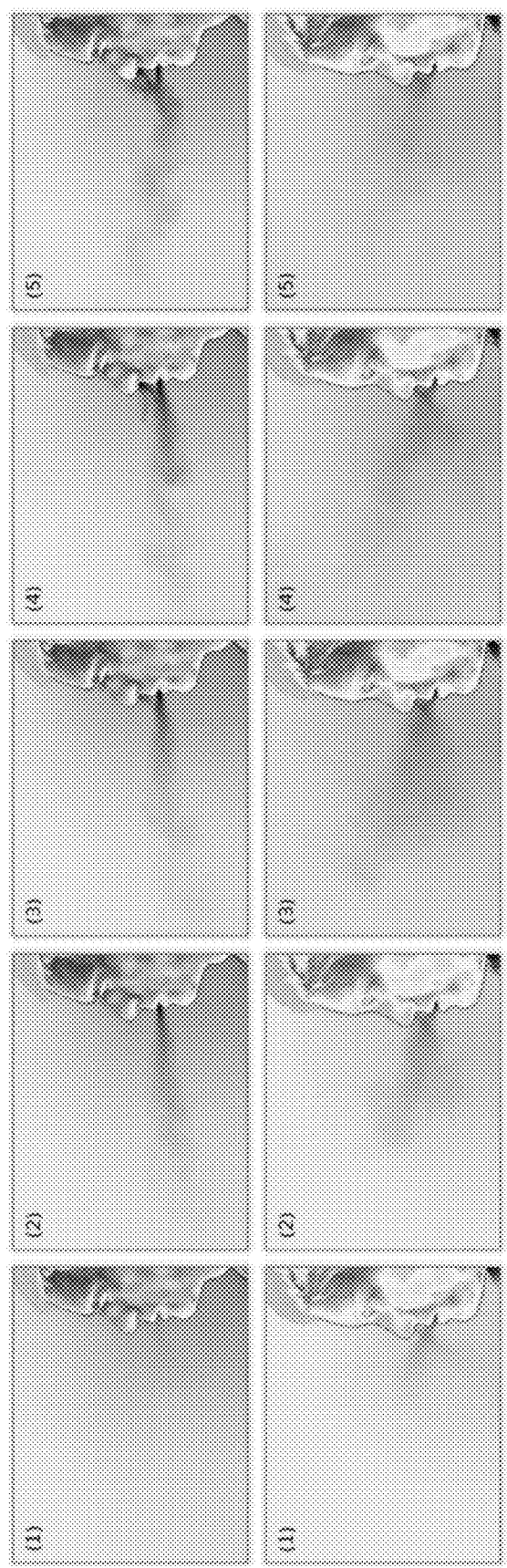
FIG. 19 is an example of an image sequence of two individuals' exhale patterns generated using various embodiments of the present technology.

Various embodiments introduce a method that is composed of two primary contributions: (1) provide a method for identifying the ideal view alignment to minimize the impact of background heat sources to actively avoid them and (2) introduce a new method for extracting exhale signatures even when other heat sources significantly interfere with the $CO_2$ signature. These methods allow us to optimize the camera using a robotic articulated system to obtain the best viewing angle possible for the application and if there is not an ideal perpendicular cross-section, some embodiments introduce the concept of thermal $CO_2$ exhale flow segmentation to separate exhale signatures from the surrounding background environment. FIG. 19 is an example of an image sequence of two individuals' exhale patterns generated using various embodiments of the present technology.

$CO_2$ Exhale Flow Segmentation

In current $CO_2$ imaging methods, extraction of the exhale signature using an infrared thermal camera requires an ideal cross-sectional view that allows the heat of the exhaled $CO_2$ to be visualized across an ideal background surface that: (1) provides a uniform thermal distribution, (2) is cooler than the exhale temperature, and (3) is not thermally reflective, such as a non-metallic matte surface. From the distinct thermal values presented by the exhale in front of this surface, the thermal distribution of the $CO_2$ gas can be easily visualized. Based on this visualization setup, current methods use this ideal viewpoint to provide a foundation for measuring $CO_2$ concentration and breathing rate. However, there are several alternative devices that provide this level of functionality for obtaining these metrics through other devices that provide more reliable quantitative measures that can be used for respiratory analysis.

Additionally, this ideal setup is difficult to obtain in practice and limits the applicability of the approach for extended data collection sessions or long-term sleep studies. This is because the ideal viewing angle can be difficult or impossible to obtain in a practical clinical environment, especially for long-term studies that incorporate patient movement. To address the lack within the practical utility of this approach, some embodiments introduce an alternative method for imaging $CO_2$ exhale flows that allows for complex and non-uniform thermal background distributions that can be used within a variety of different clinical setups to provide meaningful quantitative measurements for respiratory analysis.

Thermal $CO_2$ segmentation introduces the idea that instead of only visualizing the higher thermal values of exhaled $CO_2$ across a uniform background, some embodiments can invert the process to visualize the cooler exhale flow in front of other hotter surfaces such as the patient's face. This provides a two phase process for providing a complete visualization of the $CO_2$ gas that is independent of the background.

Figure 20:
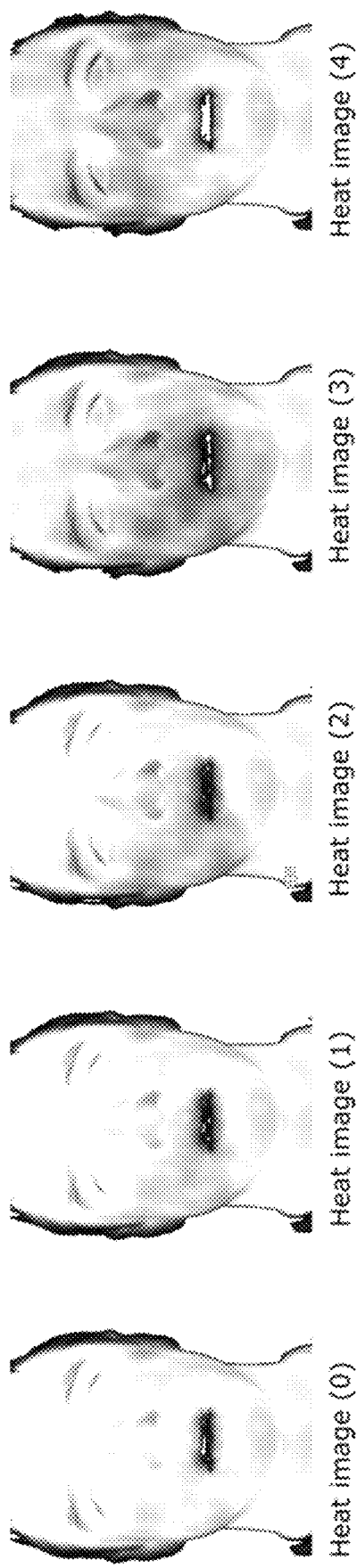
FIG. 20 is an illustration of an example of the segmented $CO_2$ exhale flow in front of a patient's face over time in accordance with various embodiments of the present technology.
Figure 21:
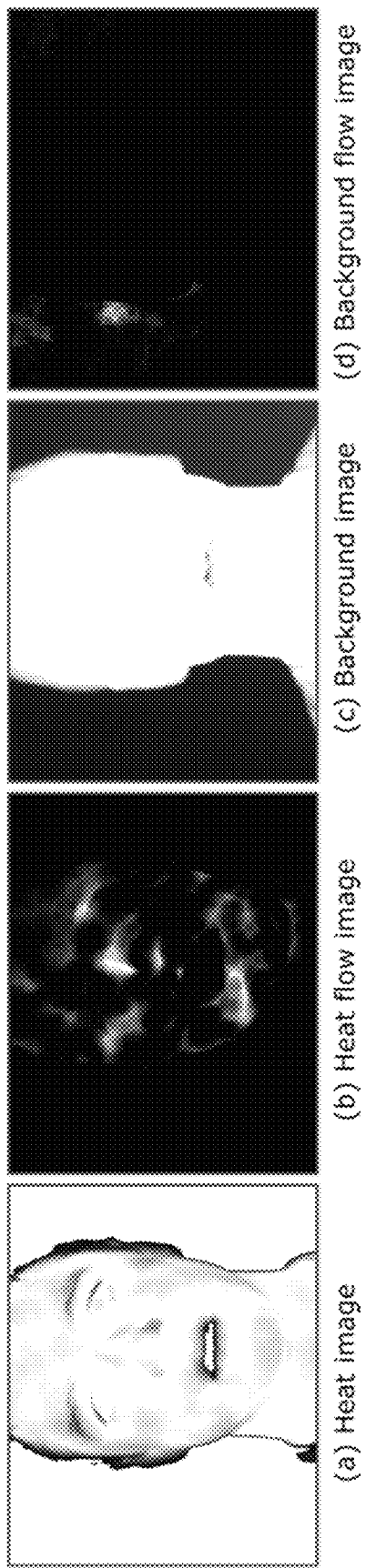
FIGS. 21A-21D illustrate an example of a composition of a segmented exhale image according to various embodiments of the present technology.

Phase one (P1) defines the extracted exhale signature using the current method to identify how the hot $CO_2$ flow is extracted from the surrounding environment. Phase two (P2) consists of two parts: (1) the masking of the cool exhale flow over any heated surface and (2) the signal separation process required to extract the $CO_2$ thermal signature from the thermal signature of the background. Unlike the process defined by P1, the thermal signature of the exhale present in P2 cannot be directly extracted from one image due to the integration of the exhale and background thermal signatures becoming mixed through the projection to the image plane of the thermal camera. To illustrate this, an exhale sequence where the $CO_2$ flow is mixed within a complex background thermal distribution (in this instance the patient's face) is shown in FIG. 20. Each image provides a static representation of how the thermally intense face is occluded by the cooler exhale particles that rapidly dissipates. Due to the difficulty of extracting the signature unique to the exhale flow, the differences between subsequent images can be analyzed in some embodiments to extract the flow behavior rather than the static signature present in each image.

Extraction of the exhale flow over the complex thermal surface is performed as the $CO_2$ distribution pattern changes over time. This provides a time-varying signature that distinctly represents the exhale flow over the background surface. This information can then be processed through a signal separation algorithm to separate the thermal signature of the face from the exhale flow, forming the foundation of the thermal exhale segmentation algorithm. The flow extraction process is illustrated in FIGS. 21A-21D.

Figure 22:
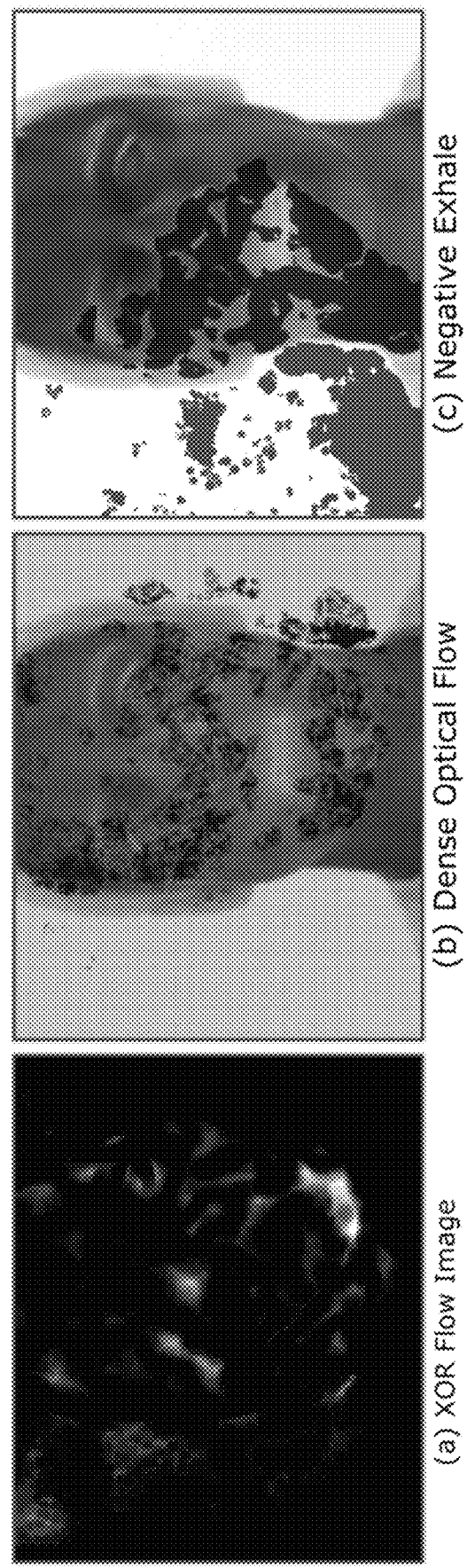
FIGS. 22A-22C illustrates an example of a dense optical flow and exhale mask obtained for $CO_2$ segmentation that may be used in various embodiments of the present technology.

The combination of the heat and background signatures can be combined to generate a complete frame of the exhale flow using an XOR operation. The resulting image will then provide the mixed exhale signature that is visible in front of background heat sources. To extract the flow behavior due to the changes over time in the XOR image sequence, some embodiments can compute the dense optical flow between each flow image. This identifies the flow characteristics that arise from the change in frame as shown in FIGS. 22A-22C.

The masked region of the image limits the analysis to the clusters within the image that contain the mixed exhale and background thermal signatures. To extract the signature of the exhale, the background thermal signature must be estimated so that it can be subtracted from the mixed signal. This process leaves an estimate of the exhale signature that can then be used to extract clinically meaningful metrics related to the respiratory characteristics of the patient.

3D Exhale Volume Reconstruction for Tidal Volume Estimation

Direct visualization of $CO_2$ exhale flows provides an intuitive method for obtaining numerous important respiratory metrics including tidal volume. However, to provide an accurate method for extracting clinically meaningful metrics for respiratory analysis, a reliable model must extrapolate dense exhale flow information into higher level abstractions and quantitative behavior traits. Tidal volume estimation is one of the primary targets for clinical evaluation of airflow and lung functionality that can be quickly performed using a number of existing devices. The problem with these existing devices is that the methods used by each device alter natural breathing behaviors. This is typically due to using either a mask or tube apparatus to measure flow which restricts airflow due to pressure differentials and requires that the patient breathe a portion of the last exhale due to the residual $CO_2$ within the tube or device. Therefore, the objective is to provide a reliable method for estimating a patient's tidal volume directly using the exhale visible within the $CO_2$ thermal image to allow for natural breathing without the use of additional devices or contact with the patient.

Figure 23:
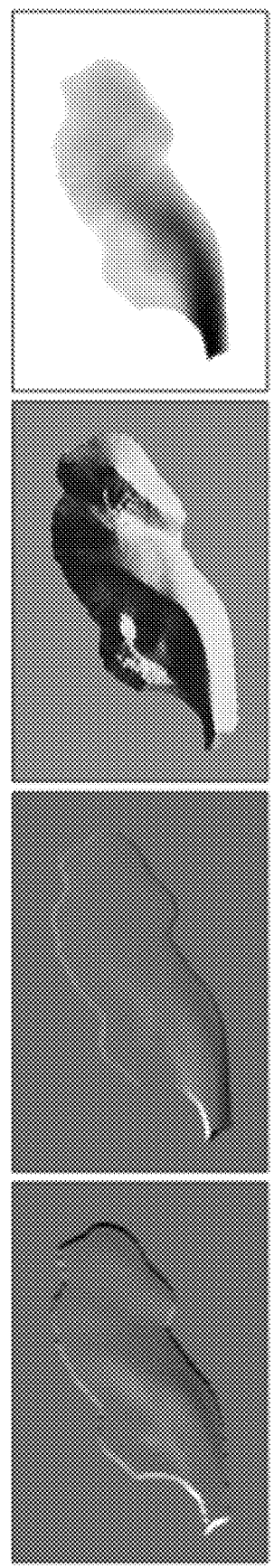
FIGS. 23A-23D illustrates an example of a reconstruction pipeline in accordance with some embodiments of the present technology.

To obtain the 3D reconstruction of the exhale volume, there are several algorithms that can be used to extrapolate the provided 2D image into a partial 3D reconstruction. Due to the projection inherent in the $CO_2$ imaging process, the depth and 3D flow characteristics of the turbulent behavior is lost. Therefore, any approximation of the 3D structure using a single device is either inferred or obtained through a machine learning estimation that attempts to correlate visualized 2D flows with 3D physical behaviors. For an analytical reconstruction, $CO_2$ density can be mapped to provide an estimate of the 3D flow behaviors illustrated by the 2D projected flow. This process is defined in FIGS. 23A-23C.

By obtaining the derivative images of the flow (dx) and (dy), computing a flow normal map that describes the flow-orthogonal vectors, and the intensity of the $CO_2$ within the exhale. In some embodiments, the x and y derivative images (FIG. 23A and FIG. 23B) are used to compute a flow normal map (FIG. 23C) that describes the volumetric characteristics of the exhale. This is then combined with the exhale flow density map to reconstruct an approximation of the 3D surface (FIG. 23D) that encloses the region of the exhale, providing an estimate of the tidal volume.

Figure 24:
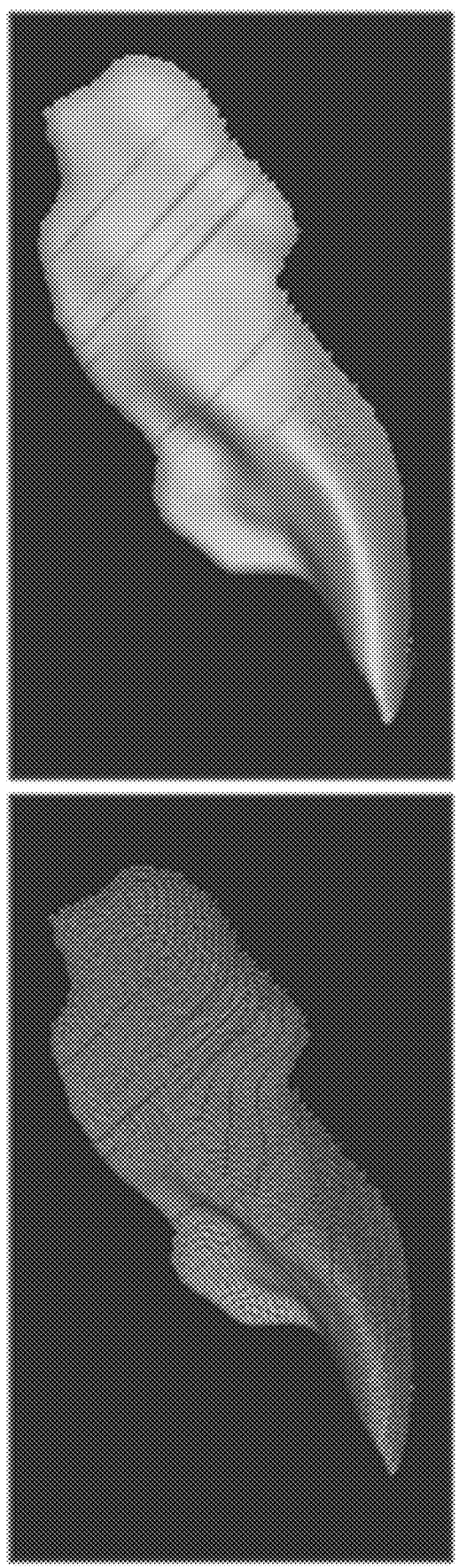
FIG. 24 illustrates an example of the exhale volume computed as a function of the flow normals and the $CO_2$ intensity to provide a reconstruction of a 3D surface that approximates the volume representing an exhale state (left) according to various embodiments of the present technology.

Building on the generated flow model, some embodiments can extrapolate an estimate of the depth as a function of the intensity of the $CO_2$ within the image and its propagation within the image to model the dissipation of the gas within an unconstrained volume (open air). The result of this process provides a dense surface approximation of the exhale volume (as a function of the dissipation cutoff). However, since some embodiments still have a loss of depth information in the actual flow, this reconstruction only provides an approximation of the actual structure in 3D space by only formulating half of the exhale structure as shown in FIG. 24. This discrete surface can then be used to form a bounded region from which some embodiments can track the tidal volume of the patient. Lighting can be used to illustrate the convex structure of the exhale shape in three dimensions Since this method is a single camera solution, there are four possible solution methods for obtaining an estimate of the tidal volume from the single image (that does not contain depth information): (1) mirror the reconstruction of the image to complete the continuous surface and enclose a volume, (2) approximate the depth of the exhale using a scaled extrapolation function, (3) introduce a thermal mirror that occupies half of the image to view the exhale from a slightly different angle to establish multiple views, or (4) employ an unsupervised machine learning method to identify the correlations between multiple exhale episodes and establish the 3D structure in space as a function of the visualized density.

Quantitative Measurements

Thermal cameras that can detect $CO_2$ are capable of providing accurate visualizations of exhale behaviors, however since the spatial representation of the exhale is projected to a 2D plane which is dependent on the camera lens and Field of View (FOV), establishing quantitative metrics of the phenomena is difficult and error prone. This is because given the intrinsic properties of the camera, the distance between each pixel is a function of the depth from which it is viewed. Therefore, metrics such as tidal volume and air flow, which require quantitative units such as Liters and Liters per second respectively require additional information that is not obtained within the $CO_2$ image.

To completely automate the process of enabling quantitative measures in the reconstructed models some embodiments employ a depth imaging device to supplement the $CO_2$ imaging camera to provide these units. This enables a profound advantage over existing solutions that only look at unit-less measurements or inaccurate correlations. This contribution allows us to bridge the gap between the technical innovation illustrated by $CO_2$ imaging and the quantitative metrics that are required for pulmonary condition diagnosis and monitoring. Additionally, these metrics are not inferred and can be directly obtained through the combined hardware solution.

Together, the $CO_2$ and depth imaging cameras can be fused (aligned) to provide a 1-to-1 correlation between both modalities. That is, for each pixel in the thermal image, some embodiments establish a correlation with a depth measurement from the depth image. This provides important information about the spatial context in which some embodiments are viewing the exhale behavior. This allows per-pixel measurements that can be integrated into the 3D exhale reconstruction to provide real-world units to the computed volume. This information is vital to the clinical deployment of the system since current pulmonary conditions are addressed through a set of known metrics and how they can be identified as abnormalities. Therefore, some embodiments introduce a multi-modal system that includes both the thermal and depth imaging to provide real-world units for obtaining quantitative metrics.

Mobile Clinical System Design

Figure 25A:
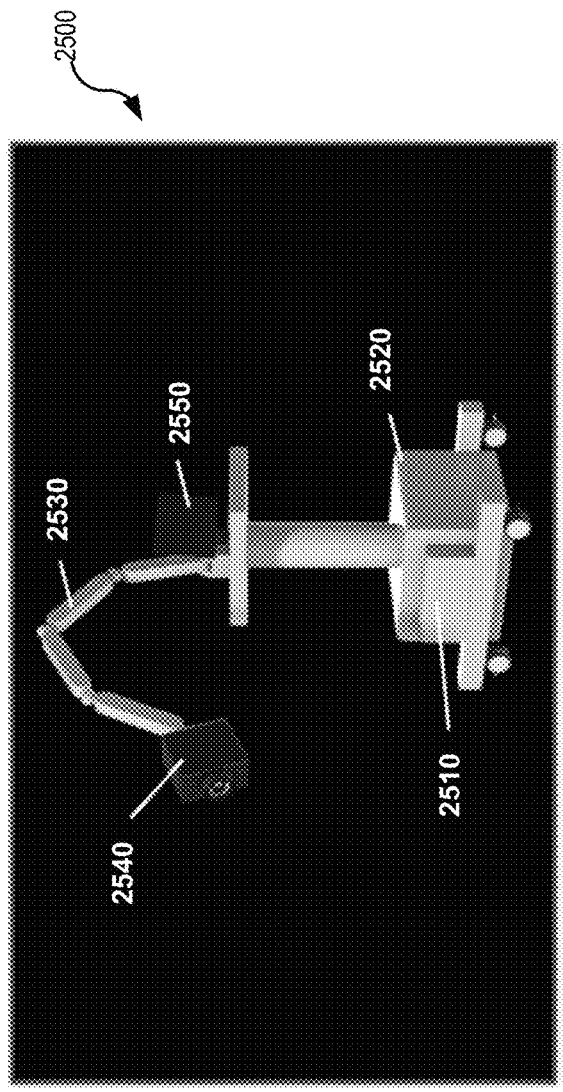
FIGS. 25A-25B illustrate an example of a system design of a modular and mobile exhale analysis solution in accordance with various embodiments of the present technology.

Clinical deployment of the system requires robust and user-friendly hardware, controls, and software to provide a semi-automated method for respiratory analysis that is highly mobile. Mobility allows the system to be used for a variety of different clinical applications such as monitoring infants and allows for precise adjustment of the camera's viewing angle. The system overview provided in FIG. 25A illustrates the configuration of the mobile system 2500. In the embodiments illustrated in FIG. 25A, the mobile system includes a mobile base 2510 allowing the system to be easily moved from room to room or positioned by a user. The mobile base can include a weighted counterbalance 2520 to ensure the articulated arm 2530 does not tip the system when extended. At the end of articulated arm 2530 is the device housing 2540 (shown in more detail in FIG. 25B). Some embodiments may include a system display 2550 to show the exhale flow and other characteristics computed by the system.

Figure 25B:
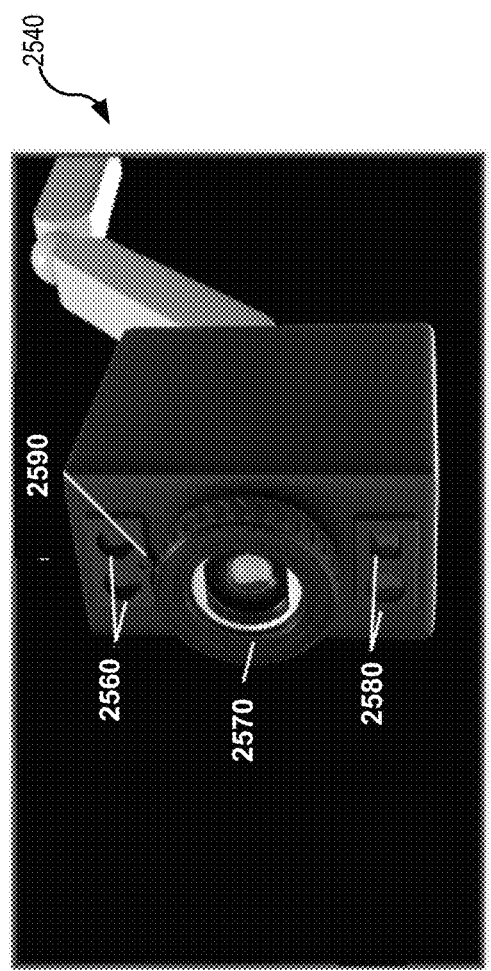

In accordance with various embodiments, the multi-modal device housing 2540 can include all of the internal cameras and calibration laser 2560. As illustrated in FIG. 25B, the device housing 2540 can enclose calibration laser 2560, thermal $CO_2$ camera 2570, depth camera 2580, and RGB camera 2590. This design incorporates the use of multiple imaging devices that can be modified to provide an ideal viewing angle of the patient during the monitoring process.

Automated Respiratory Analysis System Design

Figure 26:
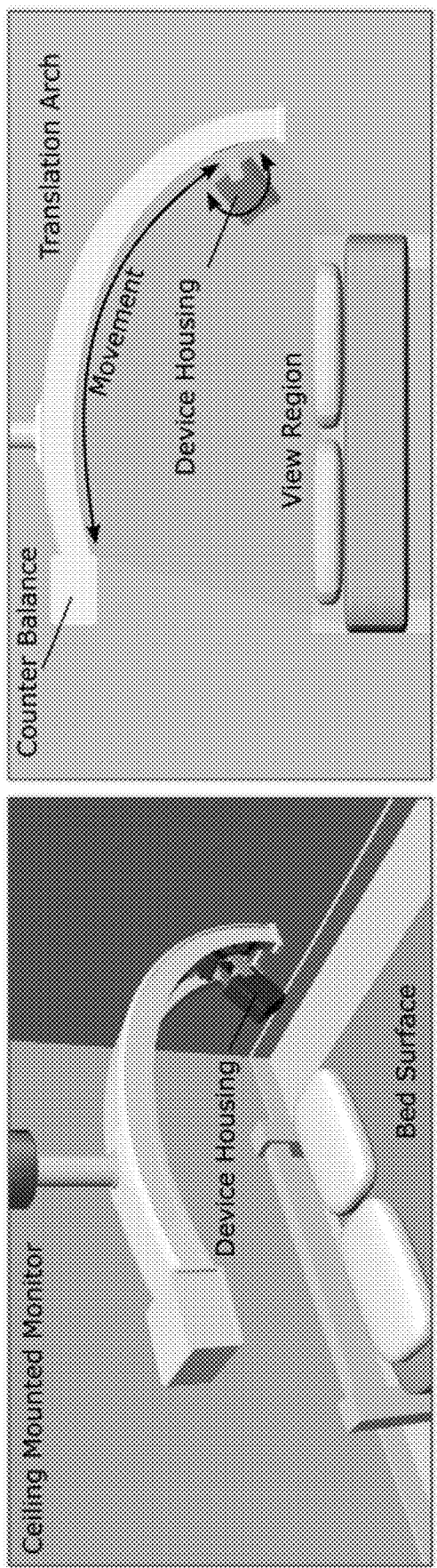
FIG. 26 illustrates an example of a ceiling mounted monitoring solution for automated respiratory analysis that may be used in various embodiments of the present technology.

Through the introduction of the multi-modal imaging devices enclosed within the device housing, some embodiments can identify and optimize towards the ideal viewing direction required to provide the most accurate measurements. To automate this process, some embodiments introduce a self-contained system that can be installed to a ceiling mount that allows for three primary modes of movement: (1) the system can be rotated about the ceiling mount, (2) the device housing is mounted to the internal track of the translation arch using a fixed track, and (3) pan and tilt motors are attached to the device housing to provide localized rotation. This configuration provides a full hemi-sphere field of movement that can be used to target the optimal viewing angle for all devices. The images in FIG. 26 provides a conceptual overview of the system. As can be seen in FIG. 26, these embodiments of the system can allow for complete hemi-spherical coverage of the view region and is controlled by three software-controlled motors. This allows translational movement in the arch, rotation about the camera's axis, and rotation about the pivot in the ceiling attachment.

In accordance with various embodiments, an orientation of the device can be automatically computed that maximizes the accuracy of the desired metrics. This may include maximizing flow characteristics or collected depth data that can be used to define the volume of the exhale in 3D space. In some embodiments, inverse kinematics may be used to obtain a specific view objective by determining the optimal joint angles required by an articulated sequence of joints that compose the mount holding the device. In some embodiments, the system can include actuators to automate the process in which the inverse kinematic structure of an articulated system can optimize the position of the device to maximize the number of pulmonological metrics that can be obtained by the system and the accuracy of each associated metric. In some embodiments, the side-view cross-section can be maximized to increase the ability to track the exhale and provide the highest accuracy of the flow and volume estimation methods.

For example, during a sleep study, the device should maintain an optimal viewing cross-section of the exhale behavior. With an articulated system of joints or movable connections, the direction of the oriented device can be adjusted to obtain an optimal cross-sectional view of the exhale based on the constraints of the bed, subject, and other monitoring session constraints. Flow information obtained may be independent of each pulmonological metric, but used to assist in the diagnostic and evaluation of pulmonological conditions.

4D Volumetric Exhale Flow Model Construction

The generation of 4D expiratory models requires a multi-stage process for segmenting, reconstructing, and, measuring exhaled $CO_2$ behaviors. To continuously capture and integrate (fuse) two-dimensional images generated by multiple integrated devices in real-time, inter-modality transformations must be defined to map the information to a consistent basis. To do this, transformations from thermal and color imaging devices are mapped to the depth image to provide an initial data aggregate that can be used to extrapolate exhale behavior characteristics to a three-dimensional spatial context. Due to the inability to receive accurate depth information throughout the exhale region (depth values will only represent background measurements), regions of the face close to the mouth are used to estimate the approximate depth of the exhale plane. From this, the distance between pixels in the data aggregate can be measured to provide an estimate of the cross-sectional area of the captured exhale flows. This information is used to relate the two-dimensional $CO_2$ flow information with the spatial measurements of the depth image.

FIG. 27 illustrates two subsequent exhale frames based on grayscale pixel intensity. The visualized exhale carbon dioxide exhibits two distinct flow patterns at the time instances $t_i$ and $t_{i+dt}$. Both the temporal and spatial derivatives of the image sequence are computed to determine the apparent flow of the exhale between these two time steps captured as separate frames.

To construct a four dimensional model of the exhale behavior, a multi-stage pipeline can be defined in some embodiments to segment the identification, segmentation, tracking, reconstruction, and measurement process. The three input video streams, represented as a sequence of images from each device, are consolidated and integrated into a multi-modal fusion model that can be defined as an aggregate of the data sources combined into multi-parameter pixel values. The multi-parameter pixel data is then used to generate several intermediate values that are used to: (1) compute the exhaled carbon dioxide movement within the image using a parallel apparent flow computation that estimates fluid movement within the thermal IR image, (2) computes the distance of relative surfaces (ex. face) to estimate the depth of the exhale plane in 3D space, (3) identifies the changes in the $CO_2$ density distribution over time, and (4) integrates this extrapolated information into a 3D model that precisely identifies the exhale at a given instance in time.

Based on this snapshot, the mixed signal (background thermal IR sources versus exhale) is then separated to obtain the $CO_2$ component of the exhale, free from other IR sources. Once the exhale contribution is isolated, the model is then consolidated into a 4D model that represents a sequence of the three-dimensional reconstructions over time. During this process, physical units are maintained to ensure that accurate measurements of respiratory behaviors can be estimated from the resulting 4D model. This enables model analysis to generate a set of pulmonological metrics that can be used to assist in a diagnostic process used to identify pulmonological conditions.

Figure 28:
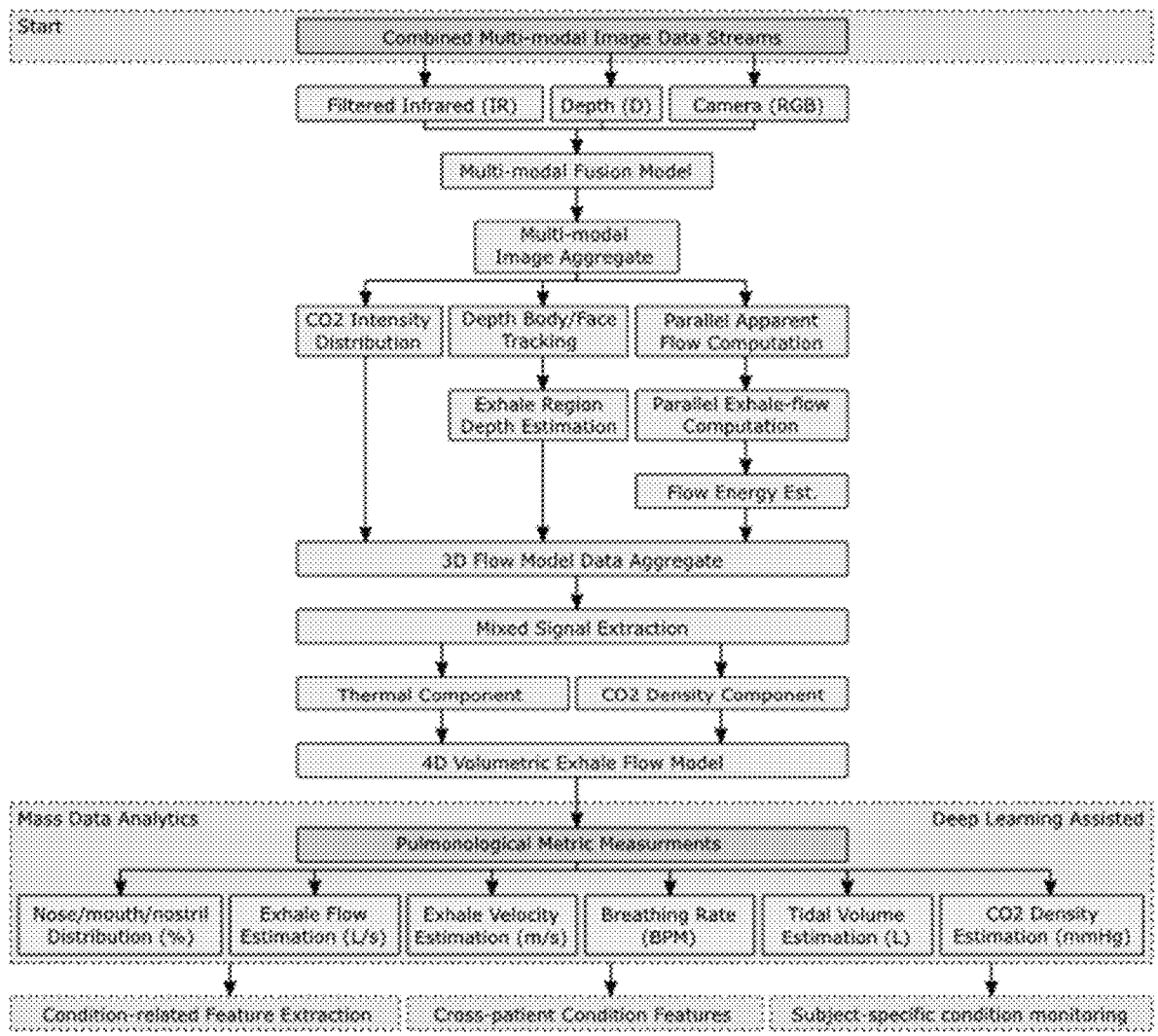
FIG. 28 is an illustration of the 4D exhale flow reconstruction pipeline used to generate clinically-relevant pulmonological metrics enabled by the solution to assist in condition diagnosis in various embodiments of the present technology.

FIG. 28 is an illustration of the 4D exhale flow reconstruction pipeline used to generate clinically-relevant pulmonological metrics enabled by the solution to assist in condition diagnosis. Based on the input stream of three devices: (1) a thermal IR camera with a spectral filter tuned to the $CO_2$ absorption band, (2) a dense depth imaging device, and (3) a normal color camera, a fused multi-modal image model is generated. This provides an aggregate of raw data that is used to extract and generate higher-level formulations of the observed exhale flow behaviors.

Based on the identification of the subject within this image, the exhale is extracted through a flow estimation process and mapped to a spatial set of 3D coordinates obtained by the depth component. This information is used to extrapolate and approximate a three-dimensional flow volume of the exhale for each time-step in the continuous image sequence. This information is then evaluated over time to establish a 4D model that characterizes all of the volume, flow, distribution, and dissipation behaviors of the exhaled gas. Using the spatial metrics obtained from the depth image and carried through this modeling process, an extended set of pulmonological metrics can be obtained by the system. This includes the measurement of the distribution between the mouth and nose during breathing monitored through this non-contact solution and the natural fluctuation between each nostril over time and represents these changes in airflow as a distribution percentage.

Based on the spatial representation of the model over time, the exhale flow is estimated in Liters per second (L/s) and also provides a basis for estimating the exhale velocity, measured in meters per second (m/s). Standard pulmonary metrics related to natural exhalation are also obtained. This includes the breathing rate in breathes per minute (BPM), tidal volume measured in Liters (L), and the $CO_2$ density estimation, measured in millimeters of mercury (mmHg). The consolidation of these metrics are then used to represent the unique features of a subjects pulmonological profile.

The pulmonological profile composed of an extended history of 4D exhale models can then be used to identify condition-related features. This results in two primary benefits: (1) the ability to perform data analytics to identify cross-subject features that commonly reoccur and (2) long-term subject condition tracking.

Figure 29:
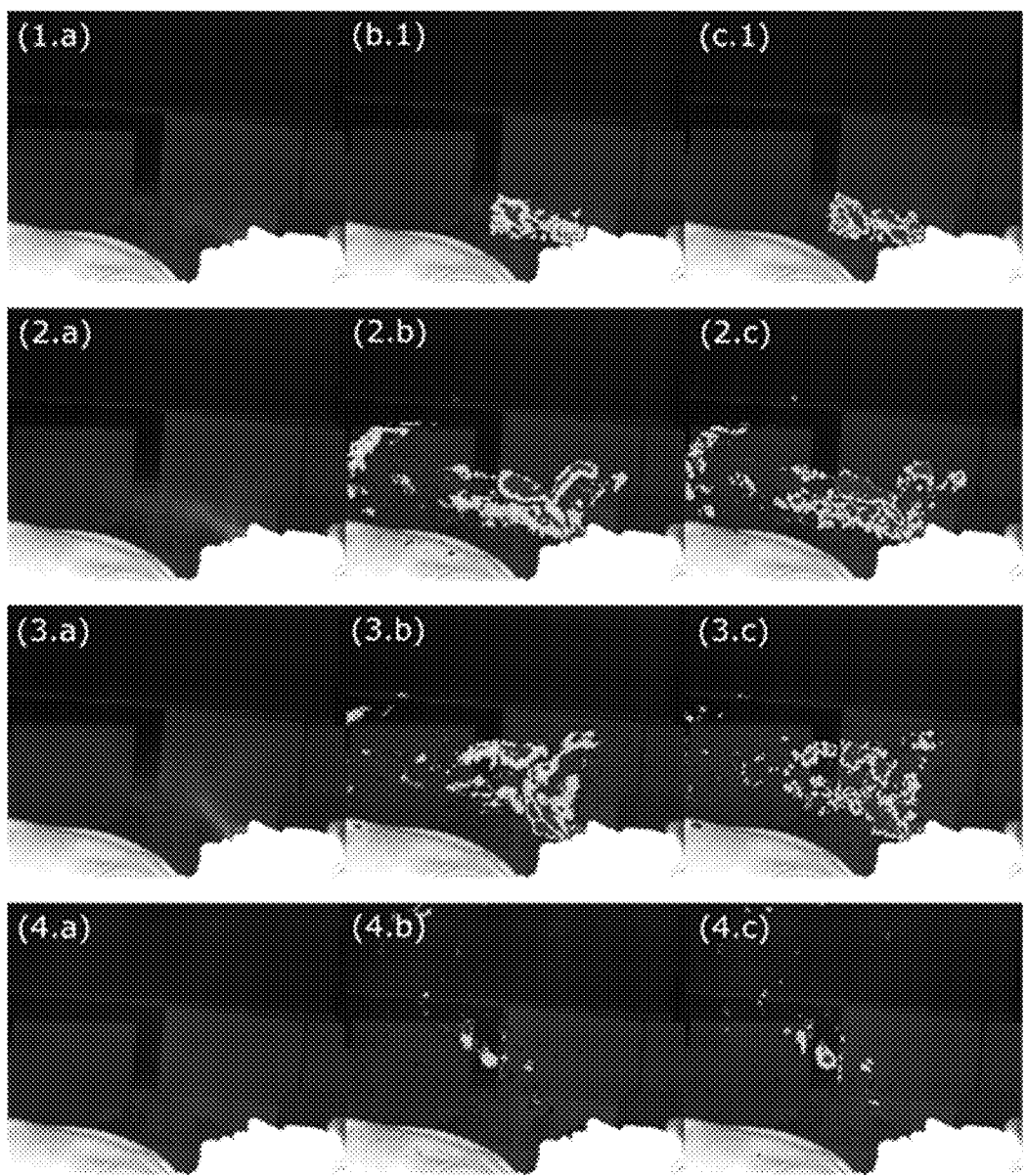
FIG. 29 is an illustration of the flow segmentation process from the original thermal IR image (a), with the flow segmentation based on a sequence of images adjacent in time (b), and the segmented fluid flow used to identify the exhale behavior in various embodiments of the present technology.

FIG. 29 is an illustration of the flow segmentation process from the original thermal IR image (a), with the flow segmentation based on a sequence of images adjacent in time (b), and the segmented fluid flow used to identify the exhale behavior. The image sequence progresses frame by frame over time from row 1 to row 4. This provides the first step in the mixed-signal process of separating the apparent exhale $CO_2$ flow from background heat sources that emit IR. The current algorithm extracts this information in real-time based on a Graphics Processor Unit (GPU) based parallel algorithm that maintains a steady sampling rate of at least 30 [Hz]. The apparent flow of the exhale is used to segment the movement and distribution of the $CO_2$ to precisely track exhale behaviors. These isolated exhale flows are then used to compute energy trace images that completely isolate the mixed exhale signal.

Figure 30:
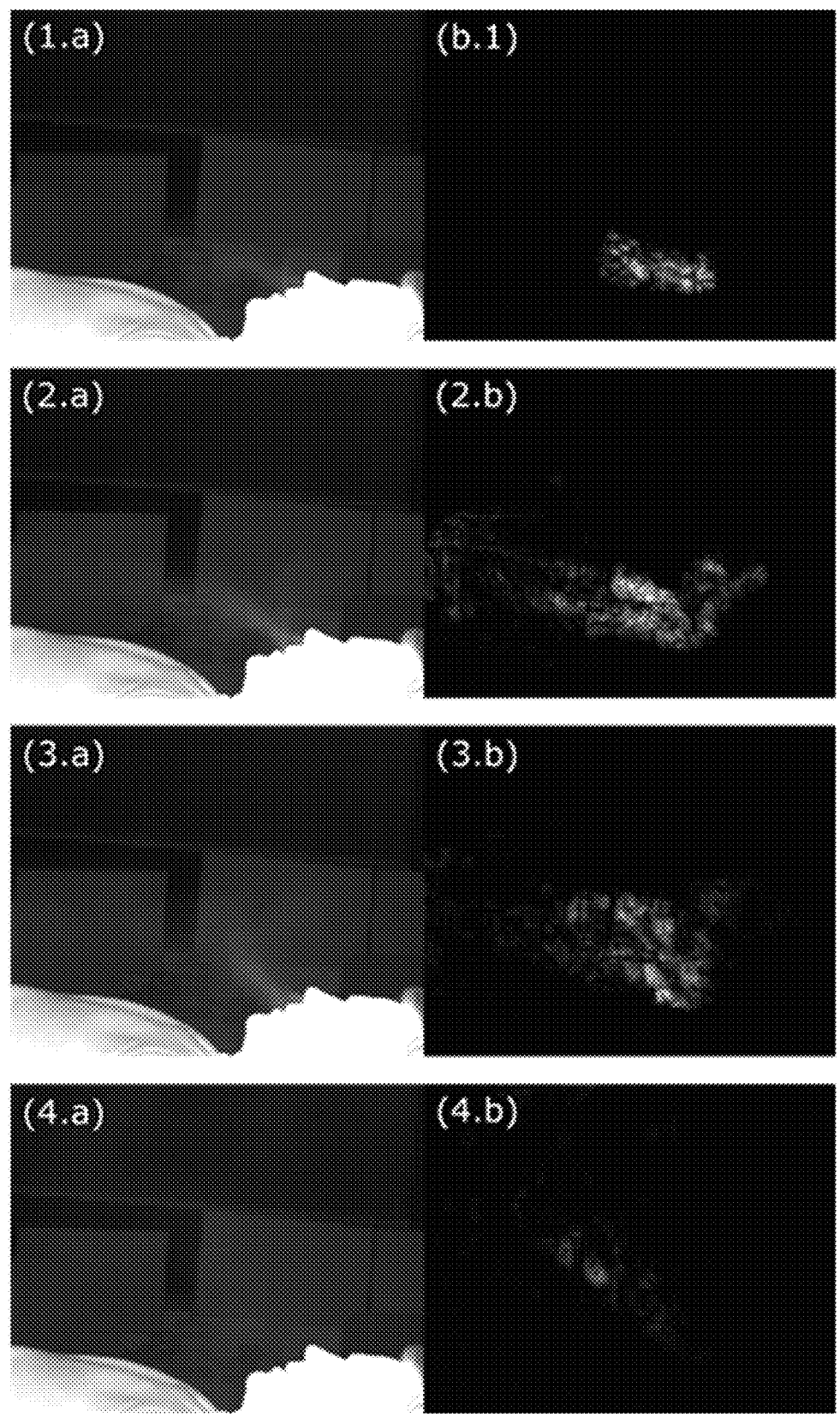
FIG. 30 illustrates captured thermal $CO_2$ images and resulting flow field region created by the exhale over time that is used to identify the distributed set of exhale turbulence that compose the entire exhale flow in accordance with various embodiments of the present technology.

In FIG. 30, the left side (a), illustrates the captured thermal $CO_2$ image. Due to the background IR sources, the energy level (pixel intensity) of the exhale is a function of both these sources and the exhale traveling across them. Using an energy function that reactivates as the fluid extraction algorithm cross over each pixel, the exhale portion receives an increased energy value. For all pixels, these energy values continuously decay. The result is a sequence (b) that clearly illustrates the segmented movement of the exhale. The result illustrates the flow field region created by the exhale over time that is used to identify the distributed set of exhale turbulence that compose the entire exhale flow.

Some embodiments provide for a method for aggregating and correlating the data generated from subject specific 4D models that are stored in large-scale databases that form a distributed model of episodic pulmonological flow and volume behaviors from different subjects. The database model can extract features from cross-subject data sets to improve the accuracy of pulmonological condition diagnosis. In some embodiments, the database entries can be defined as the 4D volumetric flow models that are recorded for each exhale from individual subjects. Deep learning methods can be applied to data sets on a per-exhale and cross-exhale basis to identify unique traits related to both an individual's unique breathing behaviors and condition specific features. These features then express a method for identifying possible traces of the identified behaviors to assist with identifying pulmonological conditions in new subjects.

In some embodiments, systems and techniques for performing large-scale data analytics and feature extraction on 4D respiratory behaviors can be included. These large-scale data analytics and feature extraction on 4D respiratory behaviors can extract condition-specific characteristics that correlate with pulmonological condition diagnosis. In some embodiments, real-time (e.g., >20 Hz) analysis of respiratory behaviors may be provided to assist in the diagnosis of pulmonological conditions. The data analytics can then be used to identify condition specific traits within a subject's exhale behaviors during the monitoring process.

In some embodiments, the database can be accessed to retrieve subject-specific information. In the instance where any pulmonological condition has been identified, new exhale flow information can be compared to data within the analytical database to track the subject's condition status. Based on a subject's unique breathing behaviors, the ability to classify models that correlate to their own data. This introduces the ability to construct a dynamic form of authentication based on the breathing behavior and exhale flow patterns unique to the individual.

Figure 31A:
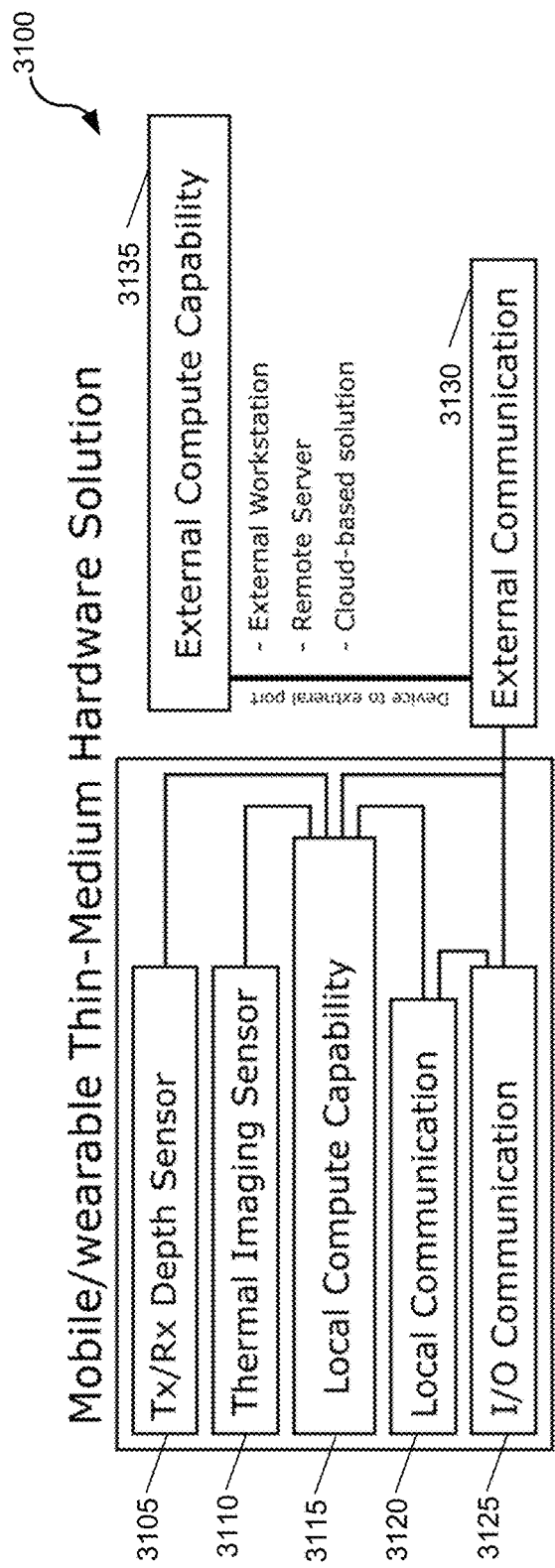
FIGS. 31A-31B illustrate block diagrams of integrated mobile configurations and sensor only configurations of the breathing analysis system.

FIG. 31A is a block diagram 3100 illustrating components of an integrated mobile configuration of the breathing analysis system. As illustrated in FIG. 31A, the mobile device can include Tx/Rx depth sensor 3105, thermal imaging sensor 3110, local compute capability 3115, local communication 3120, and I/O communication 3125 all integrated into a single, mobile form factor. Other embodiments may include additional components (e.g., a display, AR/VR components, coprocessors, and/or the like). Using I/O communication 3125, data collected from Tx/Rx depth sensor 3105 and thermal imaging sensor 3110 can be shared via external communication array 3130 with external compute capability 3135 (e.g., workstations, laptops, computer, remote servers, cloud-based solutions, etc.). In addition, some embodiments can share any processed data or computation with external compute capability 3135. In some embodiments, the mobile solution may include minimal computational abilities in order to save power. As such, imaging instructions may be received directly from external compute capability 3135, via I/O communication 3125. The imaging instructions can cause the local compute capability 3115 to control Tx/Rx depth sensor 3105 and thermal imaging sensor 3110. As such, various embodiments of the present technology may use local and/or remote computing resources to train and/or use a model correlating respiratory activity and recorded data.

Figure 31B:
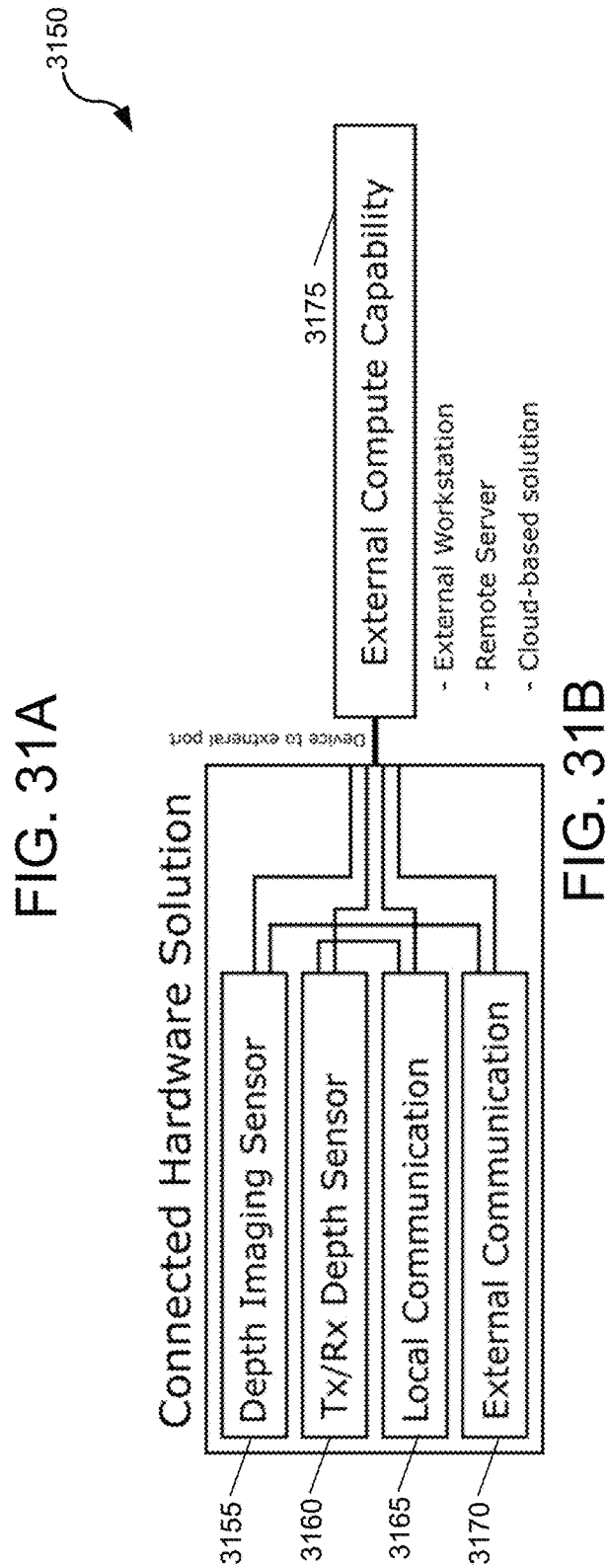

FIG. 31B illustrates a block diagram 3150 of a sensor only configuration of the breathing analysis system. In the embodiments illustrated in FIG. 31B, the breathing system may include depth imaging sensor 3155, Tx/Rx depth sensor 3160, local communication 3165, and external communication 3170. The device can connect to external compute capability 3175 where the images can be processed to generate an analysis of the respiratory behavior of the individual. In these embodiments, any significant processing is done by external compute capability 3175.

Exemplary Computer System Overview

Aspects and implementations of the breathing analysis system of the disclosure have been described in the general context of various steps and operations. A variety of these steps and operations may be performed by hardware components or may be embodied in computer-executable instructions, which may be used to cause a general-purpose or special-purpose processor (e.g., in a computer, server, or other computing device) programmed with the instructions to perform the steps or operations. For example, the steps or operations may be performed by a combination of hardware, software, and/or firmware.

Figure 32:
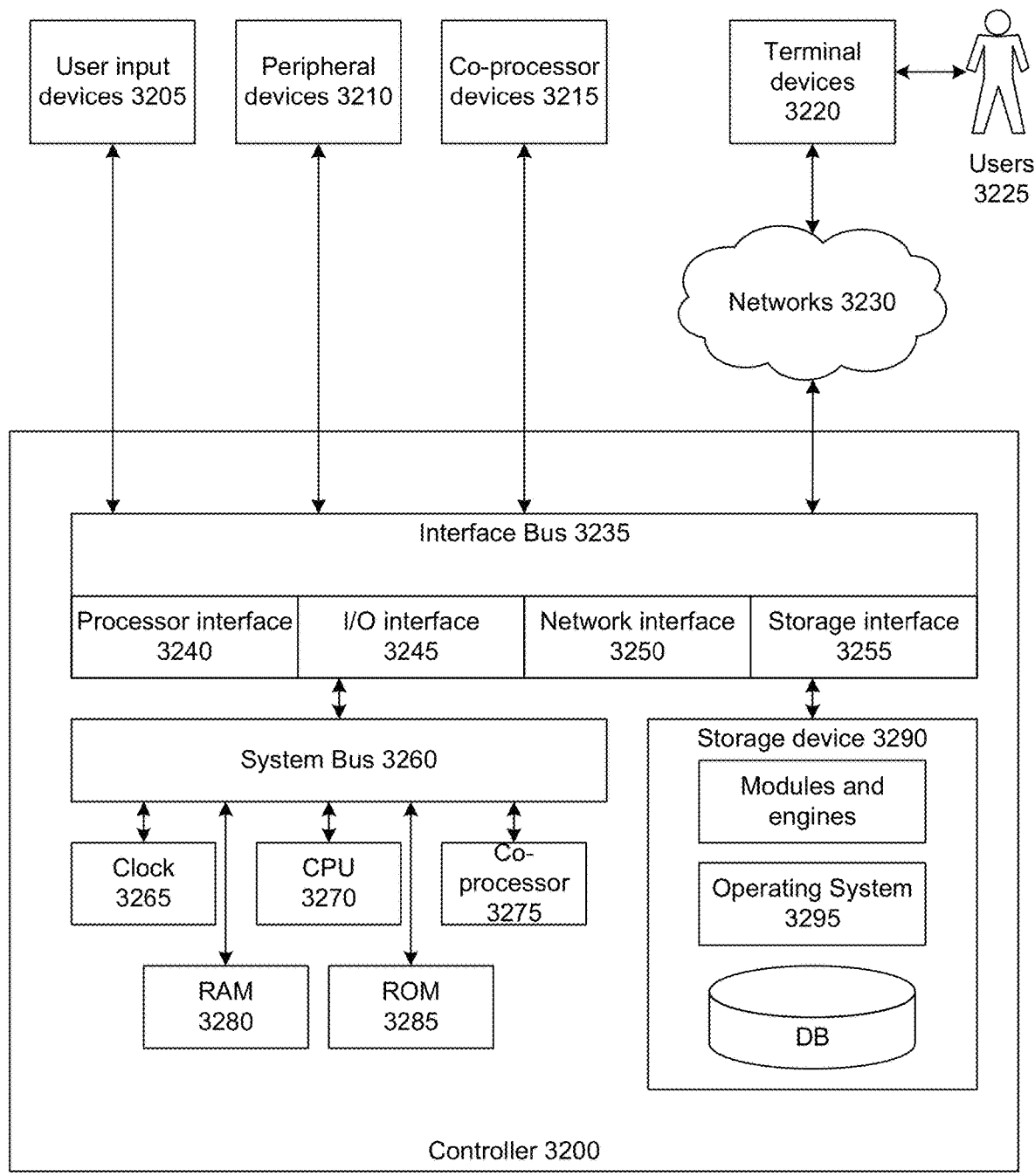
FIG. 32 is a block diagram illustrating an example machine representing the computer systemization of the breathing analysis system.

FIG. 32 is a block diagram illustrating an example machine representing the computer systemization of the breathing analysis system. The system controller 3200 may be in communication with entities including one or more users 3225 client/terminal devices 3220, user input devices 3205, peripheral devices 3210, an optional co-processor device(s) (e.g., cryptographic processor devices) 3215, and networks 3230. Users may engage with the controller 3200 via terminal devices 3220 over networks 3230.

Computers may employ central processing unit (CPU) or processor to process information. Processors may include programmable general-purpose or special-purpose microprocessors, programmable controllers, application-specific integrated circuits (ASICs), programmable logic devices (PLDs), embedded components, combination of such devices and the like. Processors execute program components in response to user and/or system-generated requests. One or more of these components may be implemented in software, hardware or both hardware and software. Processors pass instructions (e.g., operational and data instructions) to enable various operations.

The controller 3200 may include clock 3265, CPU 3270, memory such as read only memory (ROM) 3285 and random access memory (RAM) 3280 and co-processor 3275 among others. These controller components may be connected to a system bus 3260, and through the system bus 3260 to an interface bus 3235. Further, user input devices 3205, peripheral devices 3210, co-processor devices 3215, and the like, may be connected through the interface bus 3235 to the system bus 3260. The interface bus 3235 may be connected to a number of interface adapters such as processor interface 3240, input output interfaces (I/O) 3245, network interfaces 3250, storage interfaces 3255, and the like.

Processor interface 3240 may facilitate communication between co-processor devices 3215 and co-processor 3275. In one implementation, processor interface 3240 may expedite encryption and decryption of requests or data. Input output interfaces (I/O) 3245 facilitate communication between user input devices 3205, peripheral devices 3210, co-processor devices 3215, and/or the like and components of the controller 3200 using protocols such as those for handling audio, data, video interface, wireless transceivers, or the like (e.g., Bluetooth, IEEE 1394a-b, serial, universal serial bus (USB), Digital Visual Interface (DVI), 802.11a/b/g/n/x, cellular, etc.). Network interfaces 3250 may be in communication with the network 3230. Through the network 3230, the controller 3200 may be accessible to remote terminal devices 3220. Network interfaces 3250 may use various wired and wireless connection protocols such as, direct connect, Ethernet, wireless connection such as IEEE 802.11a-x, and the like.

Examples of network 3230 include the Internet, Local Area Network (LAN), Metropolitan Area Network (MAN), a Wide Area Network (WAN), wireless network (e.g., using Wireless Application Protocol WAP), a secured custom connection, and the like. The network interfaces 3250 can include a firewall which can, in some aspects, govern and/or manage permission to access/proxy data in a computer network, and track varying levels of trust between different machines and/or applications. The firewall can be any number of modules having any combination of hardware and/or software components able to enforce a predetermined set of access rights between a particular set of machines and applications, machines and machines, and/or applications and applications, for example, to regulate the flow of traffic and resource sharing between these varying entities. The firewall may additionally manage and/or have access to an access control list which details permissions including, for example, the access and operation rights of an object by an individual, a machine, and/or an application, and the circumstances under which the permission rights stand. Other network security functions performed or included in the functions of the firewall, can be, for example, but are not limited to, intrusion-prevention, intrusion detection, next-generation firewall, personal firewall, etc., without deviating from the novel art of this disclosure.

Storage interfaces 3255 may be in communication with a number of storage devices such as, storage devices 3290, removable disc devices, and the like. The storage interfaces 3255 may use various connection protocols such as Serial Advanced Technology Attachment (SATA), IEEE 1394, Ethernet, Universal Serial Bus (USB), and the like.

User input devices 3205 and peripheral devices 3210 may be connected to I/O interface 3245 and potentially other interfaces, buses and/or components. User input devices 3205 may include card readers, fingerprint readers, joysticks, keyboards, microphones, mouse, remote controls, retina readers, touch screens, sensors, and/or the like. Peripheral devices 3210 may include antenna, audio devices (e.g., microphone, speakers, etc.), cameras, external processors, communication devices, radio frequency identifiers (RFIDs), scanners, printers, storage devices, transceivers, and/or the like. Co-processor devices 3215 may be connected to the controller 3200 through interface bus 3235, and may include microcontrollers, processors, interfaces or other devices.

Computer executable instructions and data may be stored in memory (e.g., registers, cache memory, random access memory, flash, etc.) which is accessible by processors. These stored instruction codes (e.g., programs) may engage the processor components, motherboard and/or other system components to perform desired operations. The controller 3200 may employ various forms of memory including on-chip CPU memory (e.g., registers), RAM 3280, ROM 3285, and storage devices 3290. Storage devices 3290 may employ any number of tangible, non-transitory storage devices or systems such as fixed or removable magnetic disk drive, an optical drive, solid state memory devices and other processor-readable storage media. Computer-executable instructions stored in the memory may include one or more program modules such as routines, programs, objects, components, data structures, and so on that perform particular tasks or implement particular abstract data types. For example, the memory may contain operating system (OS) component 3295, modules and other components, database tables, and the like. These modules/components may be stored and accessed from the storage devices, including from external storage devices accessible through an interface bus.

The database components can store programs executed by the processor to process the stored data. The database components may be implemented in the form of a database that is relational, scalable and secure. Examples of such database include DB2, MySQL, Oracle, Sybase, and the like. Alternatively, the database may be implemented using various standard data-structures, such as an array, hash, list, stack, structured text file (e.g., XML), table, and/or the like. Such data-structures may be stored in memory and/or in structured files.

The controller 3200 may be implemented in distributed computing environments, where tasks or modules are performed by remote processing devices, which are linked through a communications network, such as a Local Area Network ("LAN"), Wide Area Network ("WAN"), the Internet, and the like. In a distributed computing environment, program modules or subroutines may be located in both local and remote memory storage devices. Distributed computing may be employed to load balance and/or aggregate resources for processing. Alternatively, aspects of the controller 3200 may be distributed electronically over the Internet or over other networks (including wireless networks). Those skilled in the relevant art(s) will recognize that portions of the breathing analysis system may reside on a server computer, while corresponding portions reside on a client computer. Data structures and transmission of data particular to aspects of the controller 3200 are also encompassed within the scope of the disclosure.

CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as a computer-readable medium claim, other aspects may likewise be embodied as a computer-readable medium claim, or in other forms, such as being embodied in a means-plus-function claim. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

What is claimed is:

1. A system for exhale gas imaging comprising:
   an infrared thermal imaging device to perform a spectral band-pass filter tuned to limit incoming wavelengths to that relevant to the visualization of exhale gaseous flow;
   an infrared imaging device that provides depth imaging;
   a visible spectrum (RGB) imaging device; and
   a computing device communicably coupled to the infrared thermal imaging device, the infrared imaging device and the visible spectrum (RGB) imaging device to perform fusion, respiratory analysis, and metric extraction, wherein the computing device receives pixel intensity values from the infrared thermal imaging device and estimates fluid flow characteristics of the exhale behavior from the pixel intensity values, wherein the fluid flow characteristics are identified independently of exact pixel values and characterized by changes of apparent flow measurements to reconstruct 4D models of exhale episodes.

2. The system of claim 1, wherein the infrared thermal imaging device is tuned to a sub-interval of the infrared portion of the electromagnetic spectrum to identify a target infrared wavelength corresponding to a desired gas.

3. The system of claim 1, wherein the computing device generates a 4D model composed of three-dimensional flow and volume information extracted through relative pixel measurements over time.

4. The system of claim 1, wherein the computing device generates a representation of exhale behavior and measurements obtained independent of image content through the isolation and extraction of flow behaviors.

5. The system of claim 1, wherein the computing device generates a localization and reconstruction of exhale flow behaviors by separating the exhale flow behaviors from identifiable objects within background images.

6. The system of claim 1, wherein the computing device generates flow and volume reconstructions by processing a sequence of images that compose a video stream of thermal CO2, depth, and RGB images.

7. The system of claim 1, wherein the thermal imaging device, infrared imaging device, and visible spectrum (RGB) imaging device are housed within a single housing that provides a targetable vision system.

8. The system of claim 7, wherein an orientation and position of the single housing is defined through inverse kinematics within adjustable segments or through a ceiling mounted system that contains rotational freedom and an attached arm with adjustable linear movement.

9. The system of claim 8, wherein the single housing includes a mobile or wearable form factor.

10. The system of claim 1, wherein the computing device constructs a 4D model of the exhale volume comprising a sequence of 3D voxel grids representative of the exhale density and volumetric distribution at points in time.

11. The system of claim 10, wherein one or more voxels of the 3D voxel grids comprise a density value and directional flow data.

12. The system of claim 10, wherein the computing device constructs a 3D voxel grid of the 3D voxel grids by seeding a voxel volume with a vector field central to the voxel volume and extrapolating outwardly from the central vector field based at least on a diffusion process applied to the 3D voxel grid and predicts 3D fluid movement from the 3D voxel grid using a prediction model that produces an estimated flow of the observed 2D behavior to 3D space.

13. The system of claim 12, wherein the computing device generates a vector field representative of apparent flow velocities based at least on differences in pixel intensity values between sequential images received from the infrared thermal imaging device, paired with flow metrics obtained from the depth imaging device.

14. The system of claim 1, wherein the computing device integrates pixel intensity values of exhale behaviors with depth measurements from a surrounding region to incorporate unit measurements in a 3D exhale reconstruction.

15. The system of claim 1, wherein the computing device performs a correlation between thermal flow and depth images as captured by the thermal infrared imaging device and the infrared imaging device providing depth imaging to estimate depth measurements.

16. A method for analyzing pulmonological function, the method comprising, by a computing device:
   obtaining, using a first imaging device, a thermal image of an exhale flow of a subject;
   isolating pulmonological behavior of the subject by identifying and tracking exhale fluid dynamics exhibited by pixel intensity values corresponding to CO2 gas flow behaviors collected by the first imaging device; and
   estimating fluid flow characteristics of the exhale behavior from the pixel intensity values, wherein the fluid flow characteristics are identified independently of exact pixel intensity values and characterized by changes of apparent flow measurements to reconstruct 4D models of exhale episodes.

17. The method of claim 16, further comprising:
   identifying and tracking exhale behaviors from thermal objects surrounding the subject; and
   constructing a three-dimensional (3D) representation of the exhale flow based on data collected via a depth camera that provides units to the volumetric measurements of the exhale flow.

18. The method of claim 16, wherein the pixel intensity values from the first imaging device represent a coupled relationship between thermal energy and CO2 emissivity, and wherein the method further comprises localizing and extracting the exhale flow from a mixed signal that represents IR emission from thermal heat sources interfering with the exhale signal due to the combined infrared wavelengths detected from the background heat source and the energy of the exhaled CO2 region.

19. A system comprising:
   a thermal camera to take an image of an exhale of a patient;
   a communications interface communicably coupled to the thermal camera to receive the image;
   a processor;
   a memory having instructions stored thereon that when executed by the processor cause the processor to generate a representation of the exhale of the patient and extract metrics for respiratory analysis, wherein the metrics include the reconstruction of exhale flows to obtain tidal volume estimates, the identification of the separation between nose and mouth exhale flows to measure nose/mouth distribution, and both the velocity and strength of exhale flows.

20. The system of claim 19, wherein the thermal camera is a CO2 thermal imaging camera and wherein the instructions when executed by the processor cause the processor to create a 3D reconstruction of exhale flows through the use of the CO2 thermal imaging camera.

21. The system of claim 20, wherein the instructions when executed by the processor create the 3D reconstruction by recording an exhale flow and extract flow characteristics and spatial metrics required to provide a direct measurement of the physiological phenomena, wherein the spatial metrics comprise depth measurements based on data captured by a depth imaging device.

22. The system of claim 19, wherein the instructions when executed by the processor further generate an inverse thermal segmentation that separates and extracts CO2 exhale signatures observed in front of other thermal sources.

23. The system of claim 19, wherein the instructions further cause the processor to generate flow vector fields based on the velocity and strength of exhale flows derived from pixel intensity values from images produced by the thermal camera.

24. The system of claim 19, wherein the instructions further cause the processor to estimate breathing strength based on a 4D model of an exhale episode derived from the flow and intensity characteristics of the measured exhale.

* * * * *